United States Patent
Zerkowski et al.

(10) Patent No.: US 12,059,351 B2
(45) Date of Patent: Aug. 13, 2024

(54) ANNULOPLASTY DEVICE

(71) Applicant: HVR Cardio Oy, Espoo (FI)

(72) Inventors: Hans-Reinhard Zerkowski, Kreuzlingen (CH); Olli Keränen, Bjärred (SE); Johannes Jung, Pforzheim (DE); Rainer Trapp, Graben-Neudorf (DE); Aryan Fallahi, Zomeding (DE); Jani Virtanen, Söderkulla (FI)

( * ) Notice: Subject to any disclaimer, the term of this patent is extended or adjusted under 35 U.S.C. 154(b) by 829 days.

(21) Appl. No.: 17/057,214

(22) PCT Filed: May 1, 2019

(86) PCT No.: PCT/EP2019/061171
§ 371 (c)(1),
(2) Date: Nov. 20, 2020

(87) PCT Pub. No.: WO2019/223975
PCT Pub. Date: Nov. 28, 2019

(65) Prior Publication Data
US 2021/0212826 A1    Jul. 15, 2021

Related U.S. Application Data

(63) Continuation-in-part of application No. 15/985,460, filed on May 21, 2018, now Pat. No. 11,234,818.
(Continued)

(30) Foreign Application Priority Data

May 21, 2018   (EP) .................................... 18173459

(51) Int. Cl.
*A61F 2/24*   (2006.01)

(52) U.S. Cl.
CPC .......... *A61F 2/2445* (2013.01); *A61F 2/2409* (2013.01); *A61F 2230/0065* (2013.01);
(Continued)

(58) Field of Classification Search
CPC ........ A61F 2/24; A61F 2/2442; A61F 2/2445; A61F 2/2454; A61F 2/2448; A61F 2/246
See application file for complete search history.

(56) References Cited

U.S. PATENT DOCUMENTS 5,062,829 A * 11/1991 Pryor ...................... A61D 7/00
                                                          604/890.1
5,716,397 A *  2/1998 Myers ................... A61F 2/2445
                                                          606/1
(Continued)

FOREIGN PATENT DOCUMENTS

EP   2072027 A1   6/2009
WO   0203892 A1   1/2002
(Continued)

OTHER PUBLICATIONS

International Search Report for International Application No. PCT/EP2019/061171, mailed Oct. 9, 2019 (7 pages).
(Continued)

*Primary Examiner* — Seema Mathew
(74) *Attorney, Agent, or Firm* — Patent Grove AB; Tomas Friend

(57) ABSTRACT

An annuloplasty device is disclosed comprising first and second support rings being configured to be arranged as a coil in a first configuration around an axial direction, wherein the first and second support rings are configured to be arranged on opposite sides of native heart valve leaflets of a heart valve, a stiffening unit, wherein at least part of the first and second support rings comprises an interior channel configured to receive the stiffening unit, wherein insertion of
(Continued)

the stiffening unit into the interior channel increases the stiffness of the first and/or second support rings. A method of repairing a defective heart valve is also disclosed.

17 Claims, 23 Drawing Sheets

Related U.S. Application Data

(60) Provisional application No. 62/751,476, filed on Oct. 26, 2018.

(52) U.S. Cl.
CPC ............ *A61F 2250/0018* (2013.01); *A61F 2250/0029* (2013.01)

(56) References Cited

U.S. PATENT DOCUMENTS

| | | | |
|---|---|---|---|
| 6,159,240 A * | 12/2000 | Sparer | C08L 31/04 623/2.36 |
| 6,267,781 B1 * | 7/2001 | Tu | A61B 18/1492 607/101 |
| 6,964,684 B2 | 11/2005 | Ortiz et al. | |
| 7,004,958 B2 * | 2/2006 | Adams | A61B 17/0684 606/151 |
| 7,445,632 B2 | 11/2008 | McGuckin, Jr. et al. | |
| 7,942,927 B2 * | 5/2011 | Kaye | A61F 2/2445 623/2.11 |
| 8,663,322 B2 * | 3/2014 | Keranen | A61F 2/2448 623/2.37 |
| 8,734,507 B2 * | 5/2014 | Keranen | A61F 2/2448 623/2.37 |
| 8,778,021 B2 * | 7/2014 | Cartledge | A61F 2/2445 623/2.37 |
| 9,056,009 B2 * | 6/2015 | Keranen | A61F 2/2409 |
| 10,595,995 B2 * | 3/2020 | Keränen | A61F 2/2409 |
| 11,554,014 B2 * | 1/2023 | Keränen | A61F 2/2445 |
| 2003/0069593 A1 * | 4/2003 | Tremulis | A61F 2/2445 623/2.11 |
| 2003/0191528 A1 * | 10/2003 | Quijano | A61F 2/2448 623/2.37 |
| 2004/0225353 A1 * | 11/2004 | McGuckin, Jr. | A61F 2/2421 623/2.11 |
| 2005/0004668 A1 * | 1/2005 | Aklog | A61F 2/2448 623/2.36 |
| 2005/0288783 A1 * | 12/2005 | Shaoulian | A61F 2/2448 623/2.37 |
| 2006/0009841 A1 * | 1/2006 | McGuckin, Jr. | A61F 2/2412 623/2.11 |
| 2006/0015179 A1 * | 1/2006 | Bulman-Fleming | A61F 2/2442 623/2.18 |
| 2006/0100697 A1 * | 5/2006 | Casanova | A61F 2/2448 623/2.37 |
| 2006/0206203 A1 * | 9/2006 | Yang | A61F 2/2448 623/2.37 |
| 2008/0208330 A1 * | 8/2008 | Keranen | A61F 2/2448 623/2.36 |
| 2010/0145440 A1 * | 6/2010 | Keranen | A61F 2/2448 623/2.37 |
| 2012/0316640 A1 * | 12/2012 | Keranen | A61F 2/2445 623/2.11 |
| 2012/0316643 A1 * | 12/2012 | Keranen | A61F 2/2409 623/2.36 |
| 2015/0073537 A1 | 3/2015 | Jimenez et al. | |
| 2021/0059816 A1 * | 3/2021 | Keränen | A61F 2/2466 |
| 2021/0177596 A1 * | 6/2021 | Zerkowski | A61F 2/2445 |
| 2021/0177597 A1 * | 6/2021 | Zerkowski | A61F 2/2445 |
| 2021/0251756 A1 * | 8/2021 | Keränen | A61F 2/2448 |
| 2021/0369457 A1 * | 12/2021 | Bapat | A61F 2/2445 |
| 2022/0409371 A1 * | 12/2022 | Keränen | A61F 2/2466 |
| 2023/0000625 A1 * | 1/2023 | Keränen | A61F 2/2445 |
| 2023/0248519 A1 * | 8/2023 | Keränen | A61F 2/2448 623/2.36 |
| 2023/0255771 A1 * | 8/2023 | Keränen | A61F 2/2448 623/2.36 |
| 2023/0270551 A1 * | 8/2023 | Reed | A61F 2/2436 623/2.11 |
| 2023/0310152 A1 * | 10/2023 | Patel | A61F 2/2418 623/2.11 |
| 2024/0074859 A1 * | 3/2024 | Zerkowski | A61F 2/2448 |

FOREIGN PATENT DOCUMENTS

| | | |
|---|---|---|
| WO | 2006091163 A1 | 8/2006 |
| WO | 2007011799 A1 | 1/2007 |
| WO | 2007030063 A1 | 3/2007 |
| WO | 2008058940 A1 | 5/2008 |
| WO | 2014190329 A1 | 11/2014 |
| WO | 2016038017 A1 | 3/2016 |
| WO | 2017125170 A1 | 7/2017 |

OTHER PUBLICATIONS

Non-Final Office Action for U.S. Appl. No. 15/985,460, mailed Jul. 22, 2020 (Not Attached).

* cited by examiner

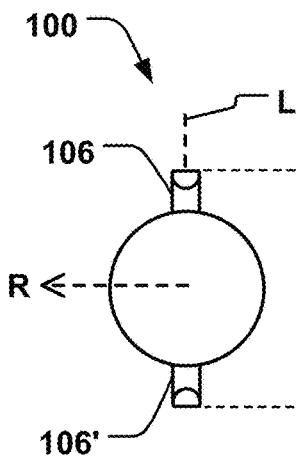
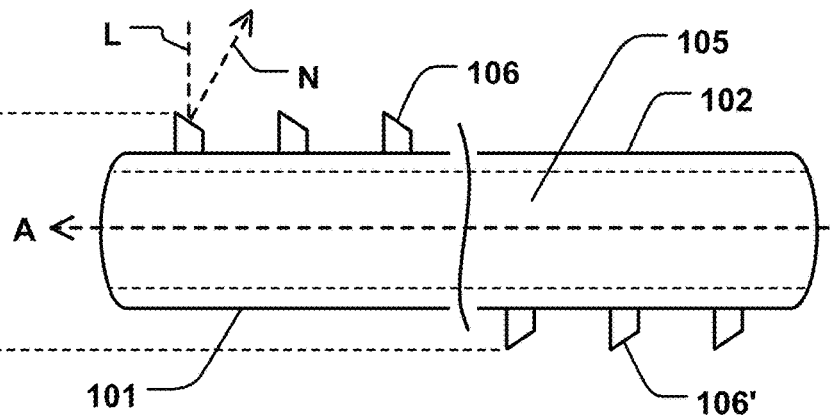
Fig. 11a          Fig. 11b
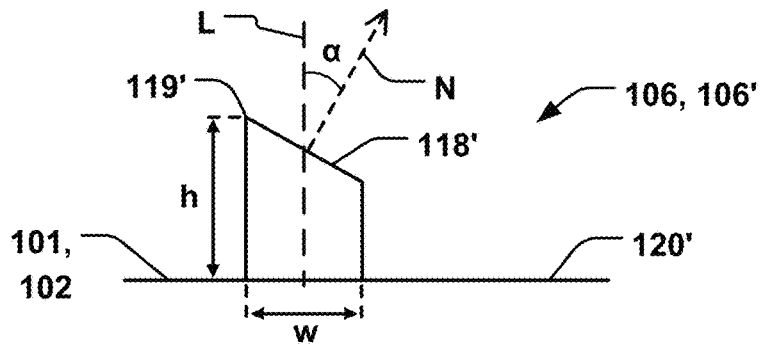
Fig. 11c
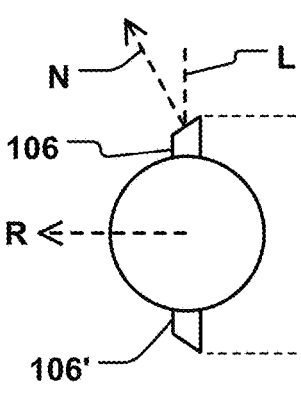
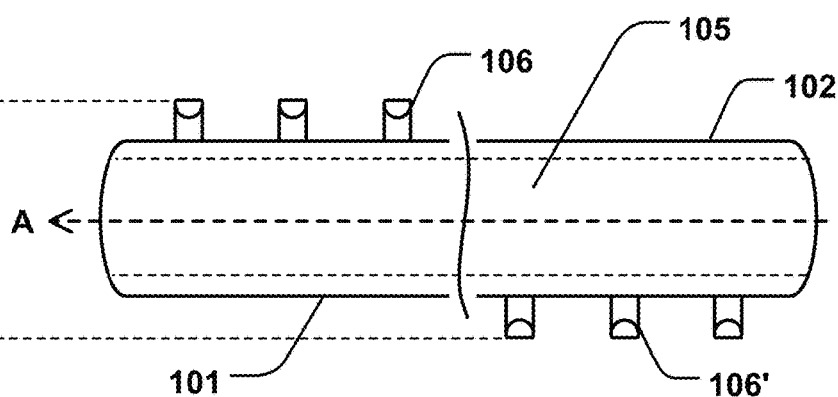
Fig. 12a          Fig. 12b

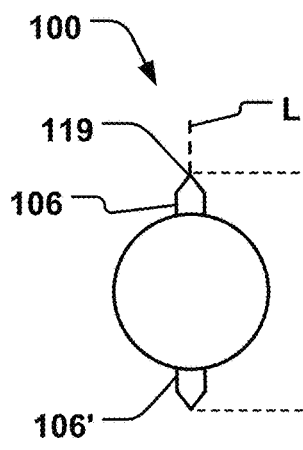 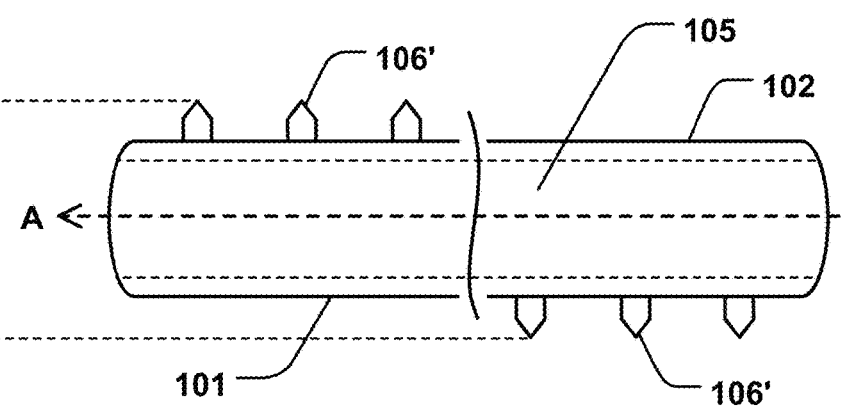
Fig. 13a        Fig. 13b
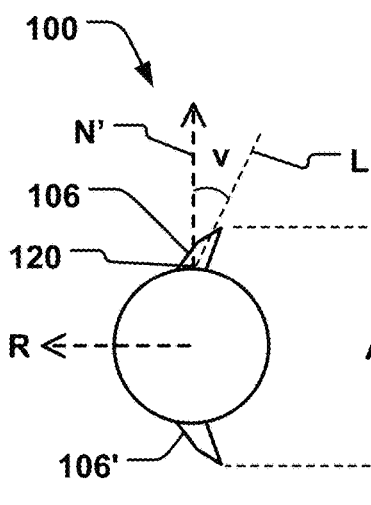 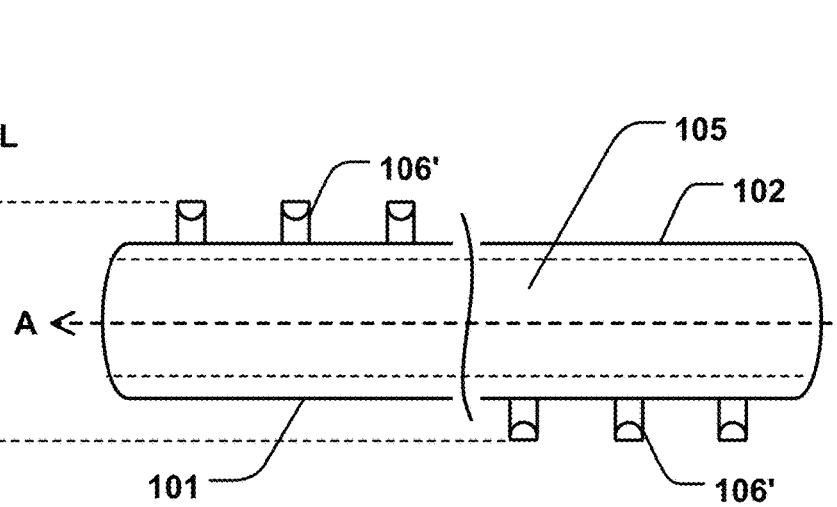
Fig. 14a        Fig. 14b

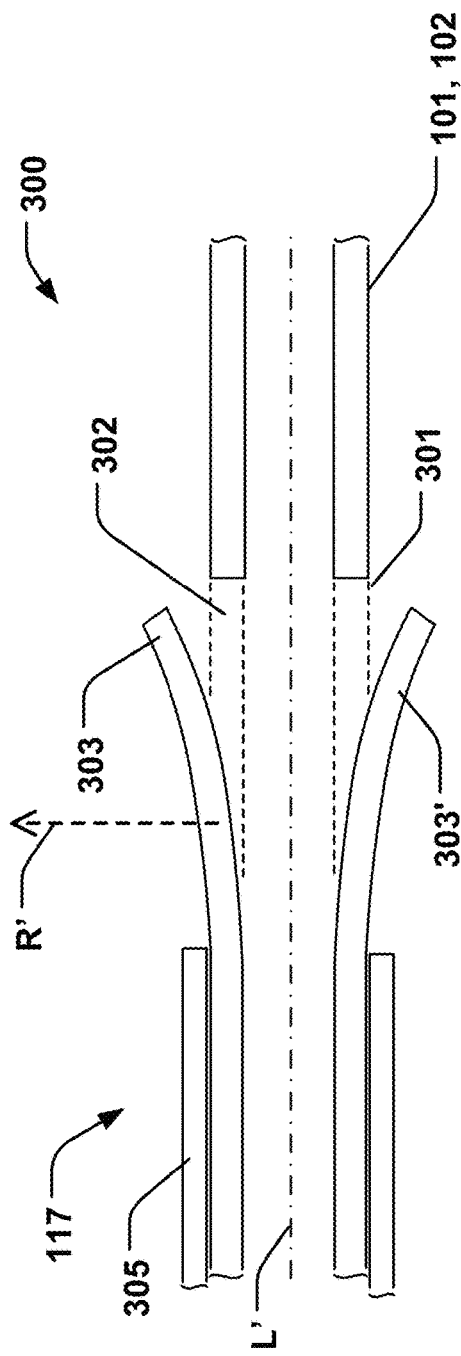
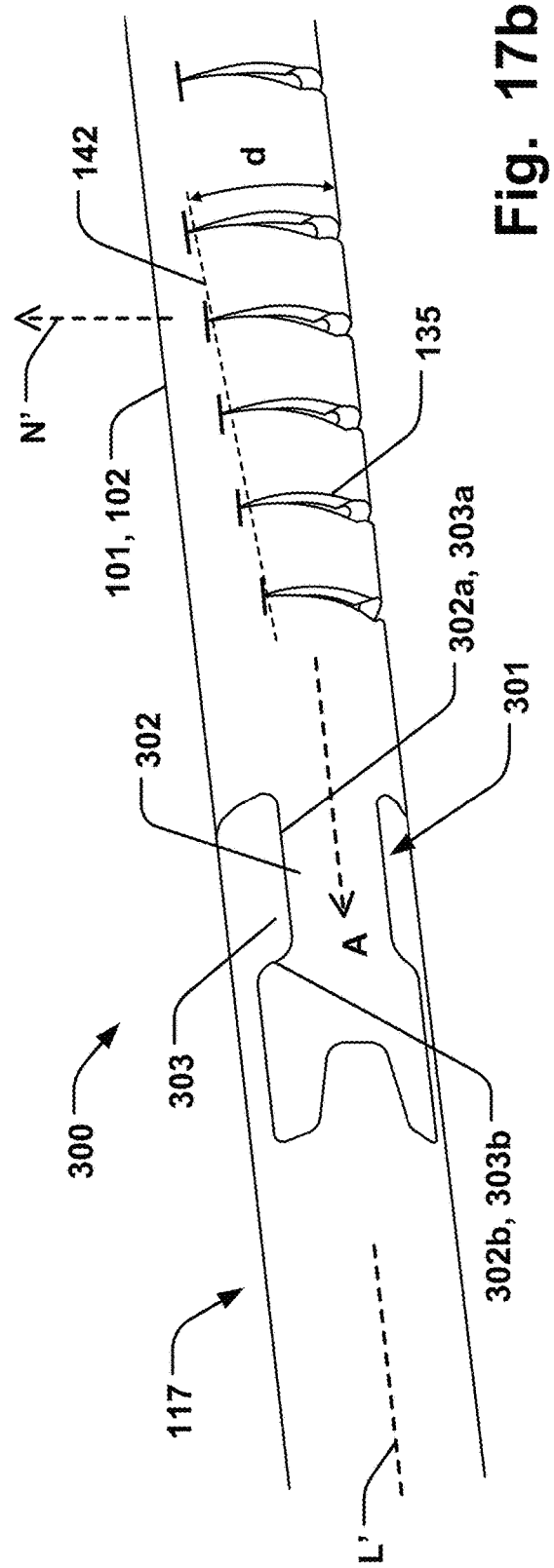

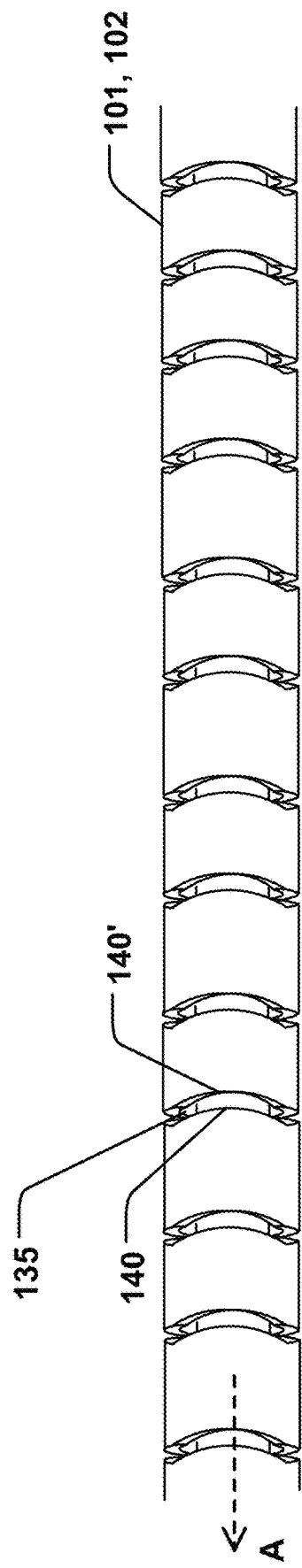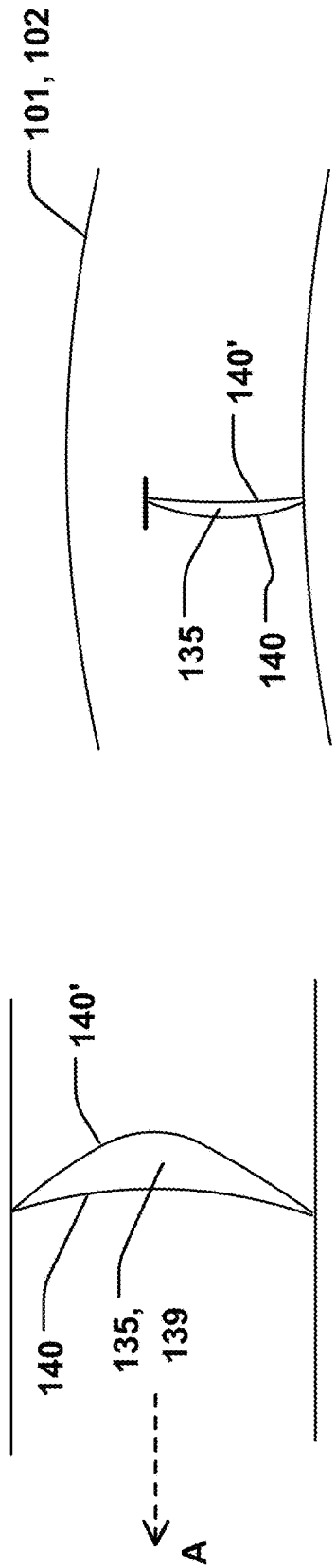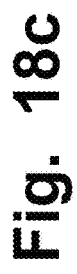

ANNULOPLASTY DEVICE

CROSS-REFERENCE TO RELATED APPLICATIONS

This application claims priority to International Application No. PCT/EP2019/061171, filed May 1, 2019 and titled "ANNULOPLASTY DEVICE," which in turn claims priority from an EP Application having application Ser. No. 18/173,459.1 filed May 21, 2018, titled "ANNULO-PLASTY DEVICE," a US Non-Provisional Patent Application having application Ser. No. 15/985,460 filed May 21, 2018, titled "ANNULOPLASTY DEVICE," and a US Provisional Patent Application having application No. 62/751,476 filed Oct. 26, 2018, titled "ANNULOPLASTY DEVICE," all of which are incorporated herein by reference in their entireties.

FIELD OF THE INVENTION

This invention pertains in general to the field of cardiac valve repair. More particularly the invention relates to an annuloplasty device, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty implant or device would be advantageous and in particular allowing for avoiding more of the above mentioned problems and compromises, and in particular ensuring secure fixation of the annuloplasty device, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided comprising first and second support rings being configured to be arranged as a coil in a first configuration around an axial direction, wherein the first and second support rings are configured to be arranged on opposite sides of native heart valve leaflets of a heart valve, a stiffening unit, wherein at least part of the first and second support rings comprises an interior channel configured to receive the stiffening unit, wherein insertion of the stiffening unit into the interior channel increases the stiffness of the first and/or second support rings.

According to a second aspect a method of repairing a defective heart valve is provided comprising positioning first and second support rings of an annuloplasty device in a first configuration as a coil on opposite sides of native heart valve leaflets of the heart valve, and increasing the stiffness of the first and/or second support rings by inserting a stiffening unit into an interior channel arranged in at least part of the first and/or second support rings.

According to a third aspect a kit comprising an annuloplasty device according to the first aspect and a delivery device is provided, wherein the delivery device comprises a locking structure to interlock with a correspondingly mating first locking structure of a delivery device connector of the annuloplasty device, wherein the locking structure of the delivery device comprises a first locking side to lock rotational movement of the annuloplasty device, when interlocked with the delivery device, around an axial direction of the annuloplasty device, and a second locking side to lock movement of the annuloplasty device along said axial direction, when interlocked with the delivery device.

According to a fourth aspect a delivery device for an annuloplasty device is provided, comprising a locking structure to interlock with a correspondingly mating first locking structure of a delivery device connector of the annuloplasty device, wherein the locking structure of the delivery device comprises a first locking side to lock rotational movement of the annuloplasty device, when interlocked with the delivery device, around an axial direction of the annuloplasty device, and a second locking side to lock movement of the annuloplasty device along said axial direction, when interlocked with the delivery device.

Further examples of the invention are defined in the dependent claims, wherein features for the first aspect may be implemented for the second and subsequent aspects and vice versa.

Some examples of the disclosure provide for a facilitated positioning of an annuloplasty device at a heart valve.

Some examples of the disclosure provide for a facilitated fixation of an annuloplasty device at a heart valve.

Some examples of the disclosure provide for a less time-consuming fixation of an annuloplasty to a target site.

Some examples of the disclosure provide for securing long-term functioning and position of an annuloplasty device.

Some examples of the disclosure provide for a reduced risk of damaging the anatomy of the heart such as the annulus or the valve leaflets.

Some examples of the disclosure provide for facilitated guidance of an annuloplasty device to an annulus of a heart valve.

Some examples of the disclosure provide for a more secure implantation of an annuloplasty device in narrow anatomies.

Some examples of the disclosure provide for avoiding interference of the annuloplasty device with the chordae of the valve leaflets.

Some examples of the disclosure provide for facilitated interlocking and release of an annuloplasty implant with a delivery device.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 11a-b are schematic illustrations of an annuloplasty implant, in a cross-sectional view (11a), and in a side view (11b), respectively, according to examples of the disclosure;

FIG. 11c is a magnified view of a retention unit in FIGS. 11a-b;

FIGS. 12a-b are schematic illustrations of an annuloplasty implant, in a cross-sectional view (12a), and in a side view (12b), respectively, according to examples of the disclosure;

FIGS. 13a-b are schematic illustrations of an annuloplasty implant, in a cross-sectional view (13a), and in a side view (13b), respectively, according to examples of the disclosure;

FIGS. 14a-b are schematic illustrations of an annuloplasty implant, in a cross-sectional view (14a), and in a side view (14b), respectively, according to examples of the disclosure;

FIG. 17a is a schematic illustration of an annuloplasty device and a delivery device, in a side view, where the delivery device releases the annuloplasty device;

FIG. 17b is a schematic illustration of an annuloplasty device and a delivery device, in a perspective view, where the delivery device is interlocked with the annuloplasty device;

FIG. 18a is a schematic illustration of a section of an annuloplasty device having slits;

FIGS. 18b-c are schematic illustrations of a slit in a portion of an annuloplasty device which undergoes a bending motion from a substantially straight shape (b) to a bent curvature (c)

DESCRIPTION OF EMBODIMENTS

Figure 1A:
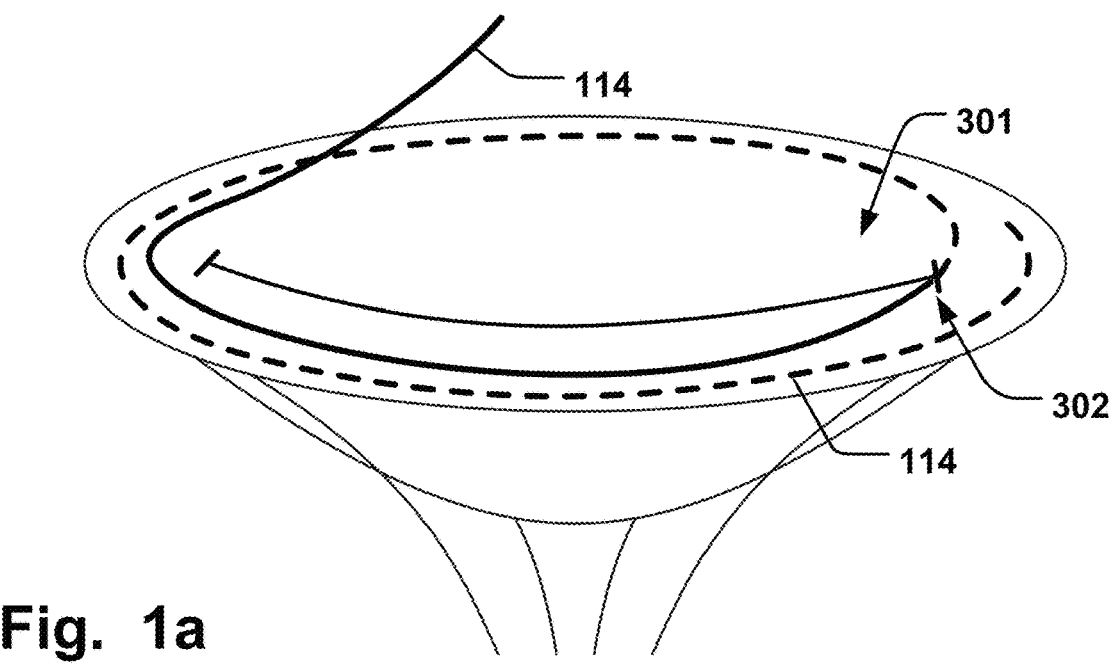
FIGS. 1a and 1c are schematic illustrations of a guide wire (end section thereof in FIG. 1b) arranged at opposite sides of the leaflets of a heart valve.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 3A:
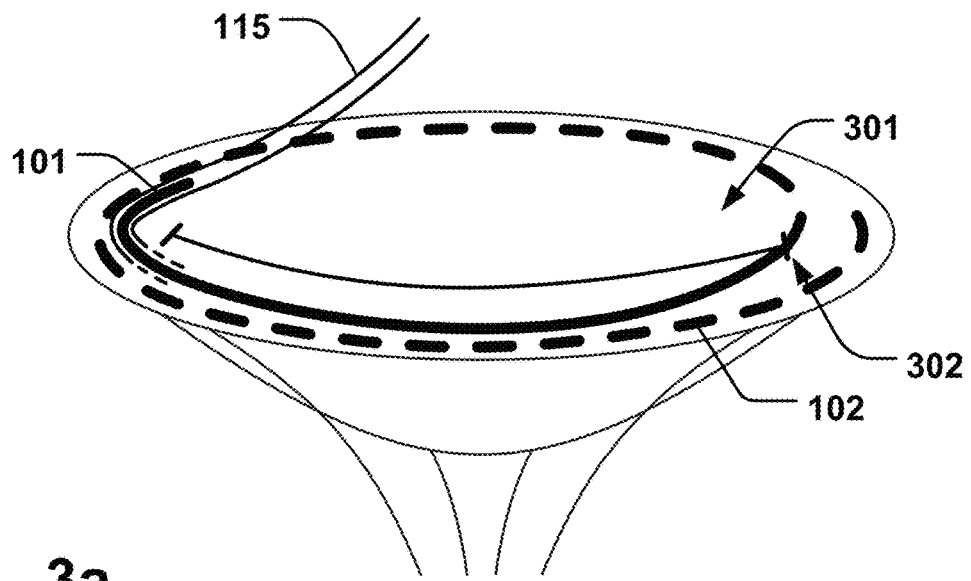
FIGS. 3a and 3d are schematic illustrations of first and second support rings of an annuloplasty device and a surrounding sheath arranged in a coiled configuration on opposite sides of heart valve leaflets, according to an example.
Figure 3B:
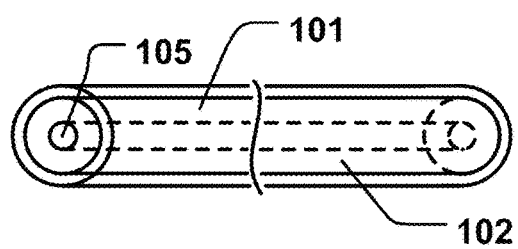
FIGS. 3b and 3c are schematic illustrations, in cross-sectional views, of support rings of an annuloplasty device arranged in a surrounding sheath.
Figure 3C:
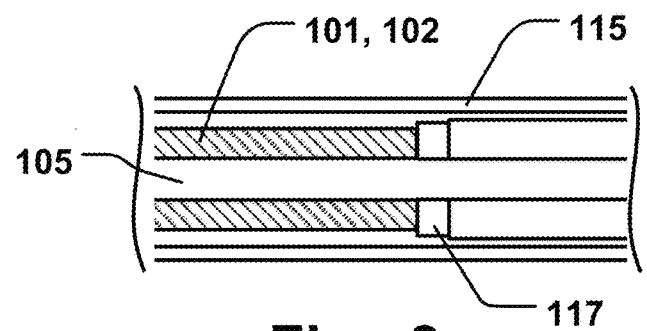
Figure 3D:
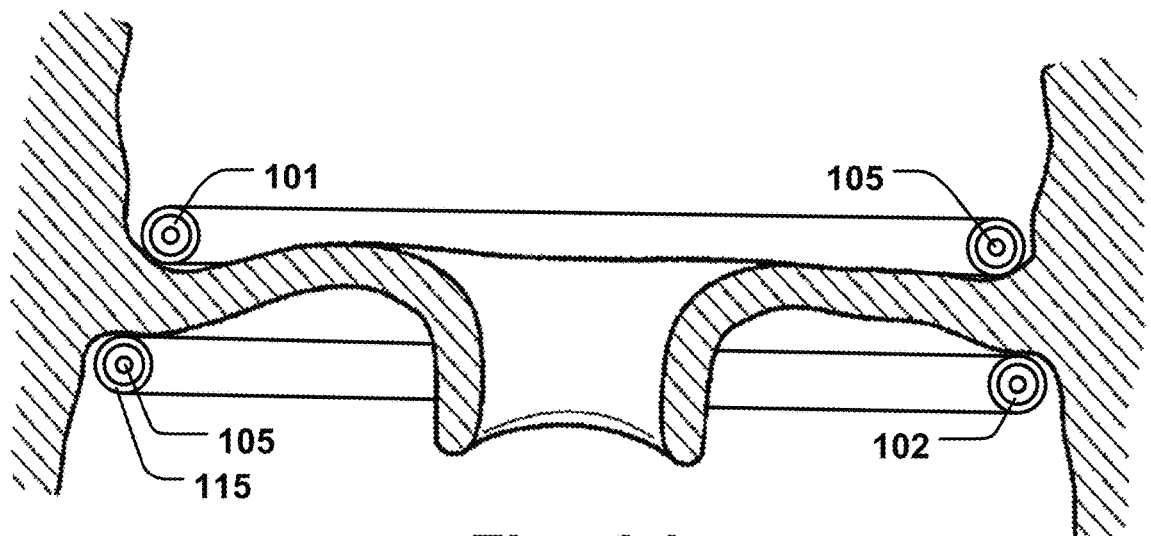
Figure 4A:
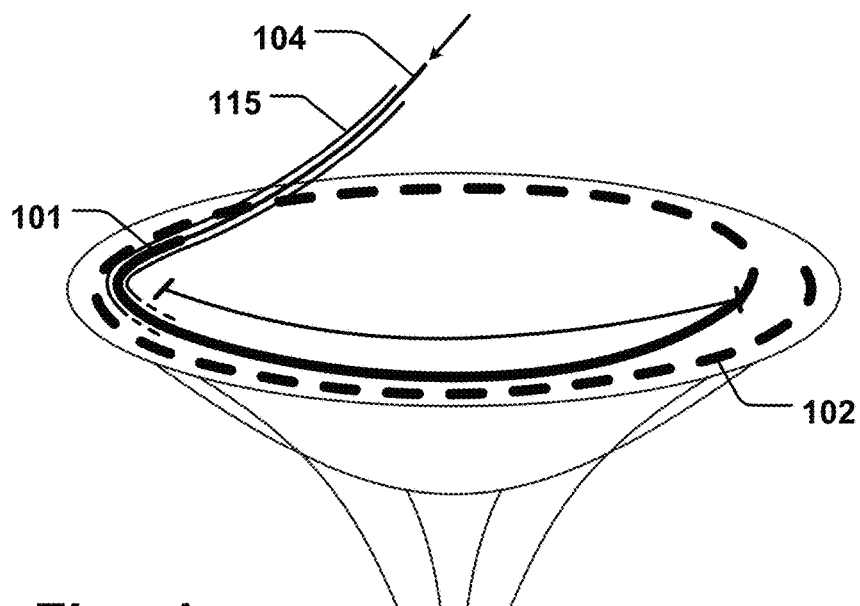
FIGS. 4a and 4d are schematic illustrations of a stiffening unit inserted into an interior channel of first and second support rings when arranged in a coiled configuration on opposite sides of heart valve leaflets, and a surrounding sheath, according to an example.
Figure 4B:
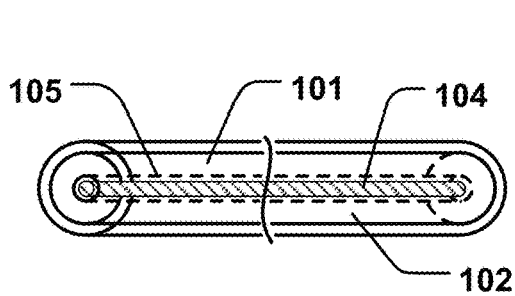
FIGS. 4b and 4c are schematic illustrations, in cross-sectional views, of a stiffening unit inserted into an interior channel of first and second support rings, according to an example.
Figure 4C:
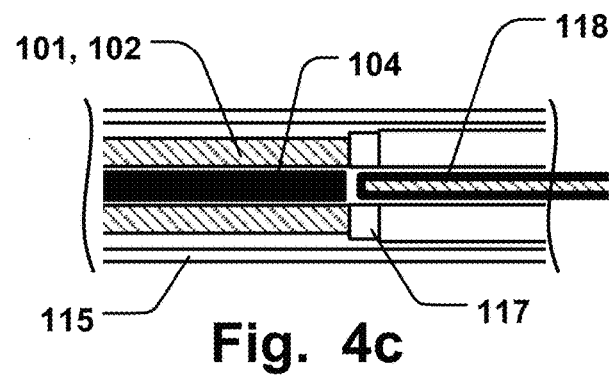
Figure 4D:
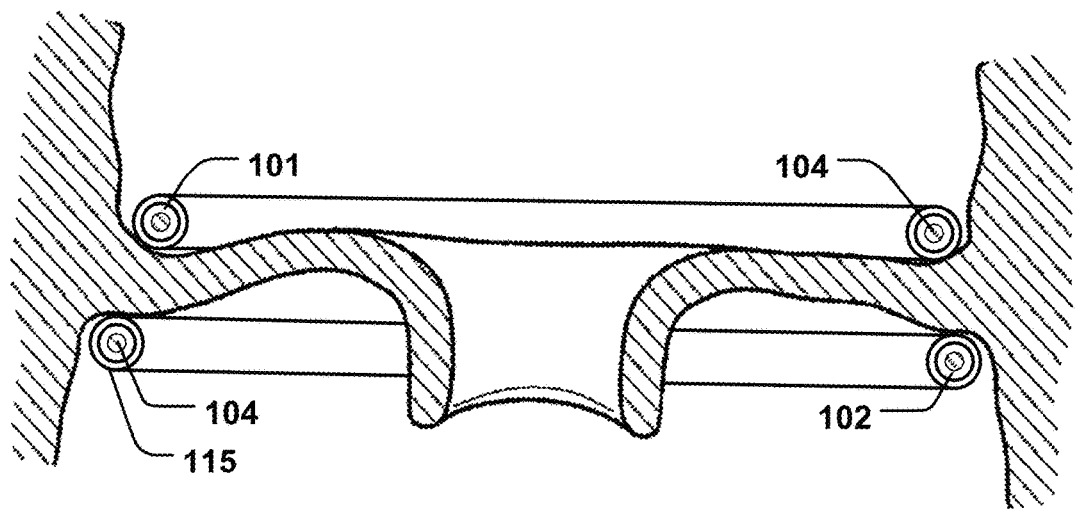
Figure 5A:
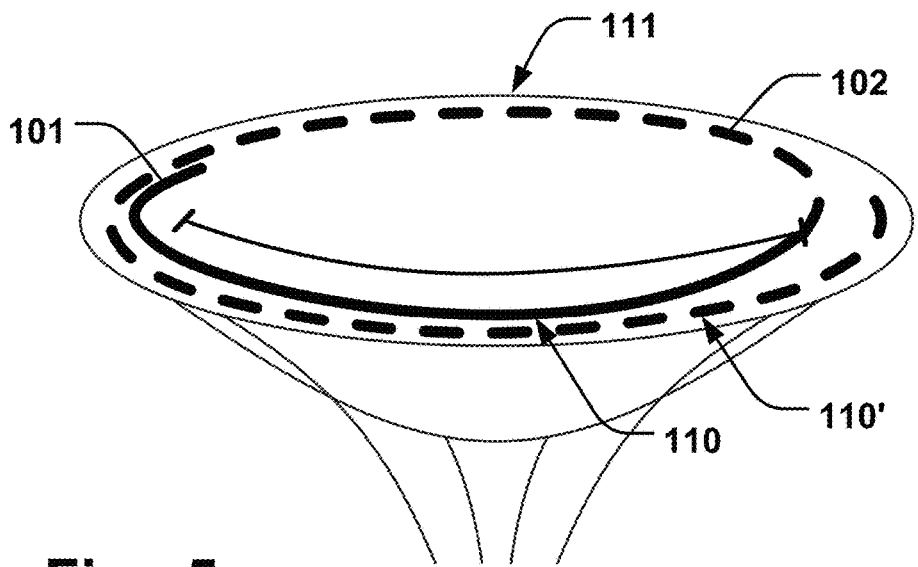
FIGS. 5a and 5d are schematic illustrations of first and second support rings, with an interior stiffening unit, arranged in a coiled configuration on opposite sides of heart valve leaflets, when the sheath is retracted, according to an example.
Figure 5B:
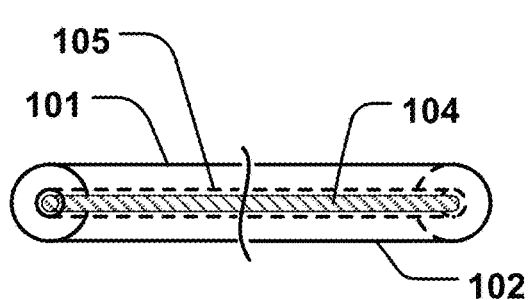
FIGS. 5b and 5c are schematic illustrations, in cross-sectional views, of a stiffening unit inserted into an interior channel of first and second support rings, according to an example.
Figure 5C:
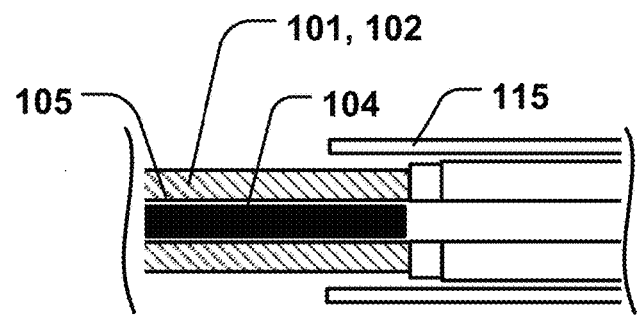
Figure 5D:
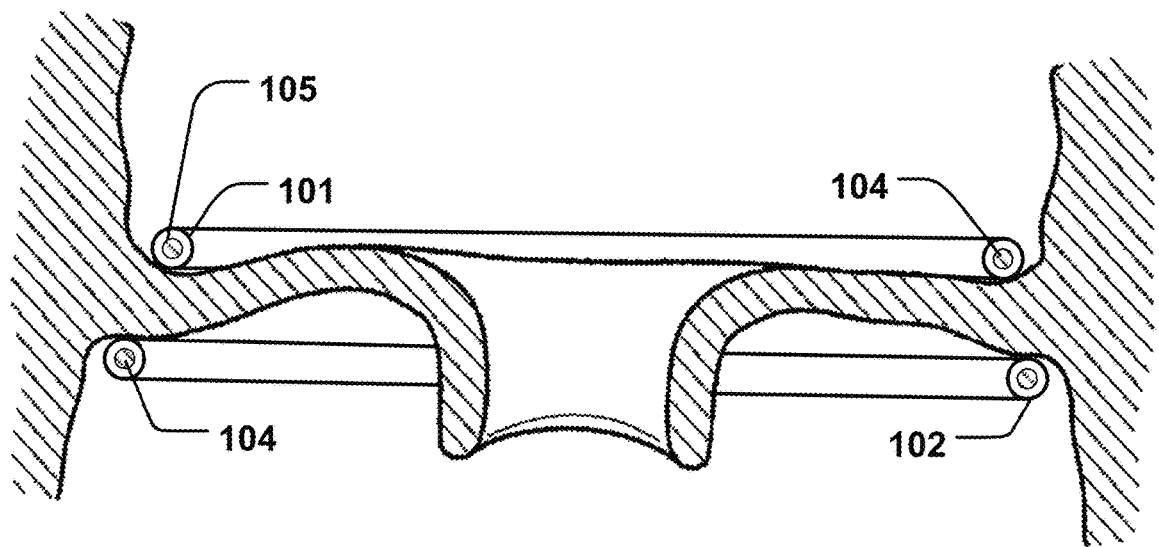
Figure 9A:
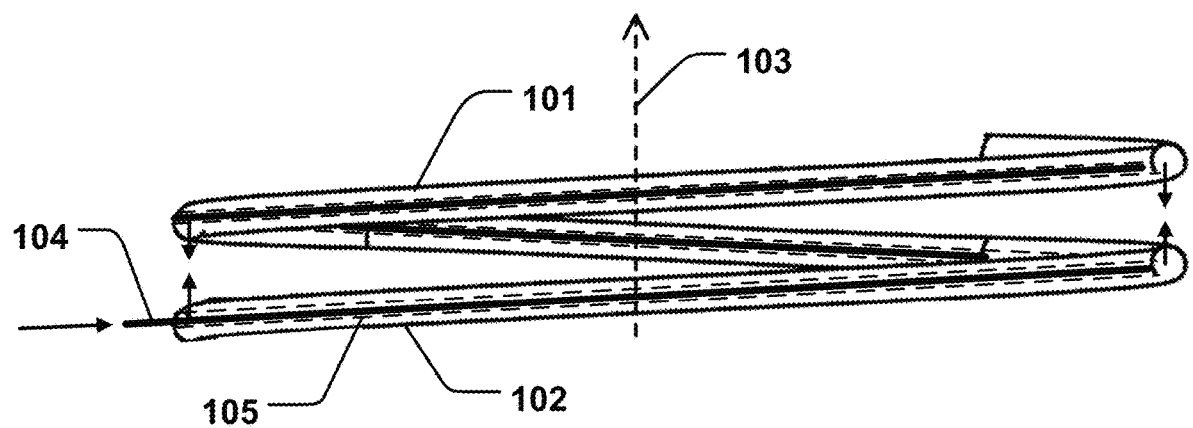
FIG. 9a is a schematic illustration of an annuloplasty device comprising an interior channel, in a side view, and a stiffening unit arranged in the interior channel, according to an example.

FIG. 9a is a schematic illustration of an annuloplasty device 100 comprising first 101 and second 102 support rings being configured to be arranged as a coil in a first configuration around an axial direction 103. The first and second support rings 101, 102, are configured to be arranged on opposite sides of native heart valve leaflets 301 of a heart valve, as illustrated in e.g. FIGS. 3a and 3d. As shown in FIG. 3d, the first support ring 101 may be arranged on an atrial side of the heart valve, and the second support ring 102 may be arranged on a ventricular side (also shown with dashed lines in FIG. 3a). The first support ring 101 thus extends along the annulus of the heart valve. The first and second support rings 101, 102, are connected to form a coil- or helix shaped ring. The coil extends through the valve opening at a commissure 302 thereof, as schematically illustrated in e.g. FIG. 3a. The annuloplasty device 100 further comprises a stiffening unit 104, where at least part of the first and second support rings 101, 102, comprises an interior channel 105 configured to receive the stiffening unit 104. FIGS. 5b, 5c, and 5d, show an example where a stiffening unit 104 is arranged in an interior channel 105 of the annuloplasty device 100. In this example, the interior channel 105 extends through both the first and second support rings 101, 102, and the stiffening unit 104 may thus extend through both said rings 101, 102. The stiffening unit 104 may thus be arranged as an interior coil inside the interior channel 105. It is conceivable however that the interior channel 105 and the stiffening unit 104 may extend through only one of the first and second support rings 101, 102. FIGS. 3b-d show the support rings 101, 102, with the interior channel 105 before the stiffening unit 104 has been positioned therethrough. FIG. 3c show a schematic delivery device 117 connected to a proximal end of the annuloplasty device 100, which may be a proximal end of the first support ring 101. The stiffening unit 104 may be positioned in the interior channel 105 via insertion through the delivery device 117, as schematically shown in FIG. 4c. In one example, an additional delivery unit 118, as shown in FIG. 4c, may be configured to deliver the stiffening unit 104 to the interior channel 105. The stiffening unit 104 increases the stiffness of the first and/or second support rings 101, 102. The rigidity of the first and/or second support rings 101, 102, is thus increased. I.e. the extent to which the rings 101, 102, resists deformation in response to an applied force is increased. In the examples shown in e.g. FIG. 5d, the stiffening unit 104 is arranged through both rings 101, 102. Thus, the stiffness of the rings 101, 102, is increased. The force by which the support rings 101, 102, pinch the leaflets from the opposite sides thereof may thus be increased, since the flexibility is reduced. This provides for facilitating a secure positioning of the first and second support rings 101, 102, at the opposite sides of the heart valve. At the same time, the support rings 101, 102, may be readily positioned at the correct position at the opposite sides of the heart valve before the stiffening unit 104 is arranged in the interior channel 105. Thus, having the stiffening unit 104 arranged in the first and second support rings 101, 102, provides for minimizing the risk of dislocation from the annulus, while providing for an easier implantation procedure. The procedure may thus be performed in a shorter amount of time. This also provides for enhancing cell growth in the vicinity of the support rings 101, 102, and a quicker healing. The device 100 as described thus also improves the long-term outcome of the valve repair procedure.

Figure 4E:
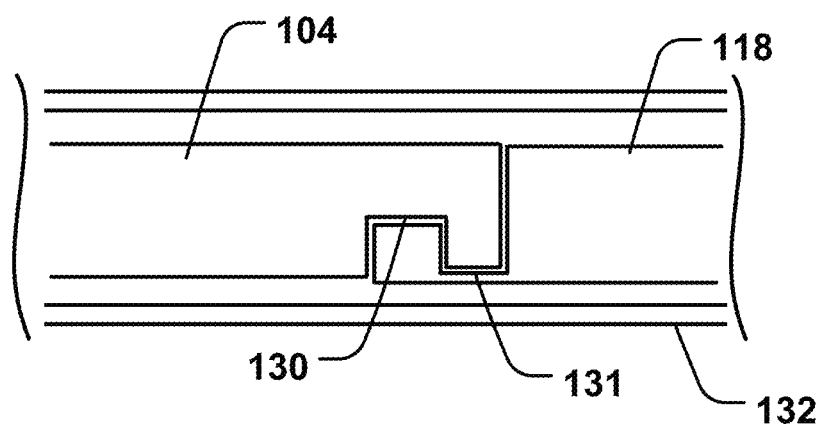
FIG. 4e is a schematic illustration, in a cross-sectional view, of a stiffening unit and a delivery unit thereof, according to an example.

FIG. 4e show one example of a delivery unit 118 configured to connect to the stiffening unit 104. In this example the delivery unit 118 and stiffening unit 104 comprises an interlocking structure 130, 131, formed as corresponding recesses 130, 131, shaped to interlock into each other. The delivery unit 118 and stiffening unit 104 may be delivered through an additional sheath 132. The sheath 132 maintains the interlocking structures 130, 131, in the locked position. When the sheath 132 is retracted, the interlocking structure 130, 131, may be released, so that the stiffening unit 104 is delivered, and the delivery unit 118 can be retracted.

Figure 8A:
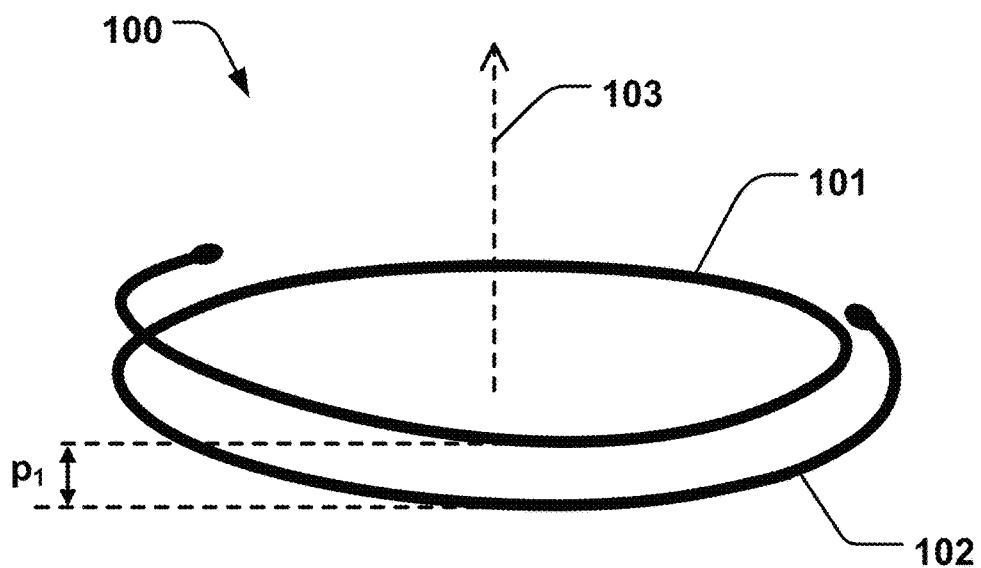
FIG. 8a is a schematic illustration of an annuloplasty device with first and second support rings separated with a first pitch distance in an axial direction, in a first configuration, according to an example.
Figure 8B:
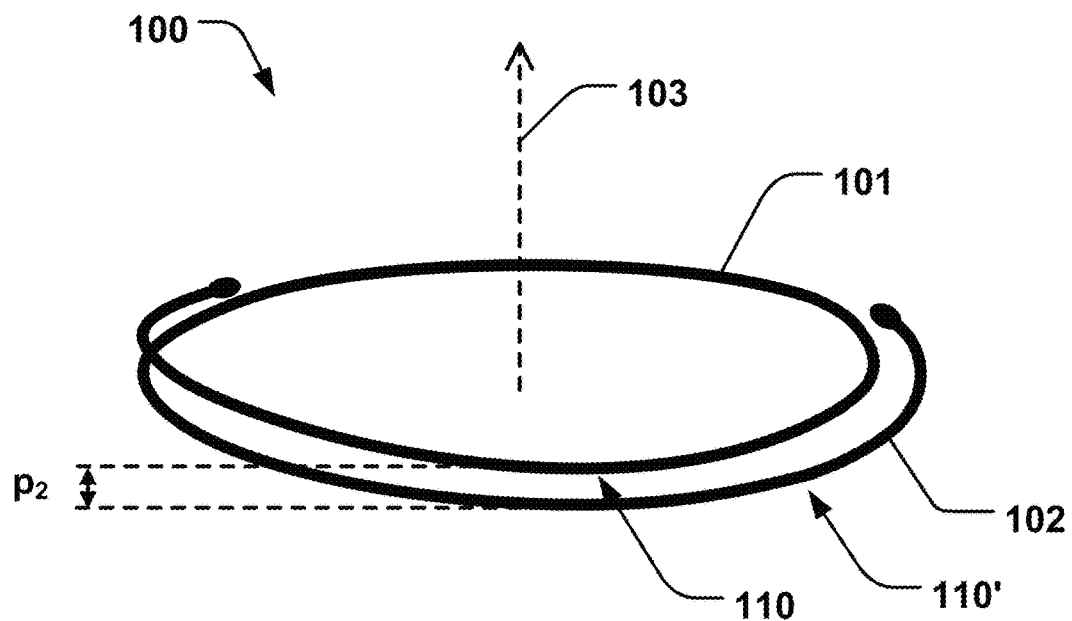
FIG. 8b is a schematic illustration of an annuloplasty device with first and second support rings separated with a second pitch distance in the axial direction, in a contracted state, according to an example.

The first and second support rings 101, 102, may be separated with a first pitch distance ($p_1$) in the axial direction 103, in a first configuration, as illustrated in FIG. 8a. The first and second support rings 101, 102, are configured to assume a contracted state having a second pitch distance ($p_2$) in the axial direction 103 being shorter than the first pitch distance ($p_1$), as illustrated in FIG. 8b. The pitch distance ($p_1$, $p_2$) is the distance of the separation (i.e. gap) between the adjacent support rings 101, 102, in the axial direction 103. The first and second support rings 101, 102, are configured to be transferable between the first configuration and the contracted state, thereby allowing for pinching the heart valve leaflets 302 when positioned in place as illustrated in e.g. FIGS. 5a and 5d. The force by which the rings 101, 102, pinch the leaflets from the opposite sides thereof may thus be increased further, providing for a secure positioning and further enhancing cell growth in the vicinity of the support rings 101, 102.

The insertion of the stiffening unit 104 into the interior channel 105 may cause the first and second support rings to transfer from the first configuration to the contracted state. I.e., the pitch distance may be reduced from $p_1$ to $p_2$ as the stiffening unit 104 is inserted into the interior channel 105, which provides for an efficient and facilitated manner by which the pitch distance can be reduced. The pitch distance of adjacent coils of the stiffening unit 104 may be varied to affect the pitch distance of the adjacent first and second support rings 101, 102, along which the stiffening unit 104 extends. Hence, the stiffening unit 104 may exert a force onto the first and second support rings 101, 102, to cause them to transfer to the compressed state (as schematically indicated by the opposed directed arrows in FIG. 9a). The stiffening unit 104 thus provides for a facilitated manipulation of the pitch distance ($p_1$, $p_2$) between the first and second support rings 101, 102.

In one example, insertion of the stiffening unit 104 into the interior channel 105 may cause the first and second support rings 101, 102, to transfer from the first configuration to the contracted state. I.e. the stiffening unit 105 may have a relaxed heat set shape in which the distance between adjacent coils of the stiffening unit 104 may correspond to the second pitch distance ($p_2$). The first and second support rings 101, 102, may have a relaxed heat set shape in which the distance between the adjacent first and second support rings 101, 102, may correspond to the first pitch distance ($p_1$). The first and second support rings 101, 102, may be flexible enough (i.e. more flexible than the stiffening unit 105) so that when the stiffening unit 105 is inserted into the interior channel 105, the first and second support rings 101, 102, are forced to also assume the second pitch distance ($p_2$), i.e. forced to the contracted state.

In one example, the stiffening unit 104 may comprise a shape-memory material. Activation of the shape-memory material may cause the first and second support rings 101, 102, to transfer from the first configuration to the contracted state. The stiffening unit 104 may thus be actively manipulated, once in place inside the interior channel 105, so that its pitch distance is varied and thereby affecting the pitch distance ($p_1$, $p_2$) of the first and second support rings 101, 102, as described above. The shape-memory material may be configured to be activated in response to an activation temperature. Hence, the temperature of the stiffening unit 104 may be changed to affect the discussed shape-change thereof.

The stiffening unit 104 may have a cross-section that allows for facilitated bending in a desired direction. E.g. the force required to bend the stiffening unit 104 in a direction in which it forms a corresponding coil shape, as the first and second support rings 101, 102, may be lower than the force required to bend in a direction in which the first and second support rings 101, 102, move to pinch the valve leaflets. A greater clamping force may thus be provided in the latter direction. For example, the stiffening unit 104 may have a rectangular cross-section, where bending is facilitated in determined directions.

Figure 16A:
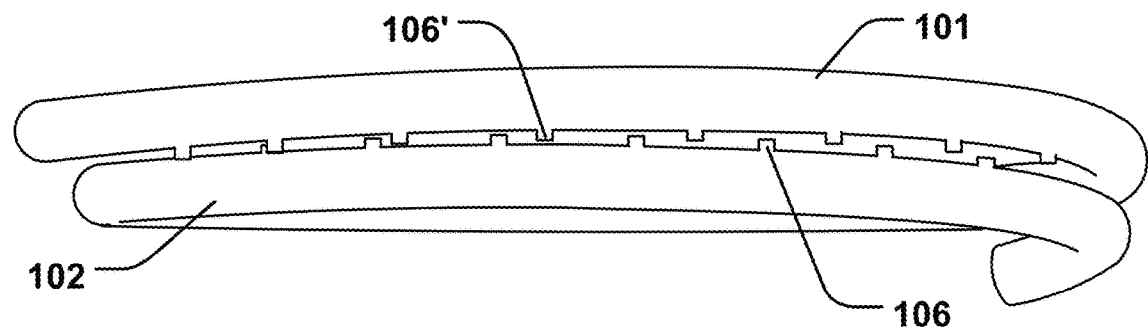
FIG. 16a is a schematic illustration of an annuloplasty device, in a side view, having oppositely arranged retention units.
Figure 16B:
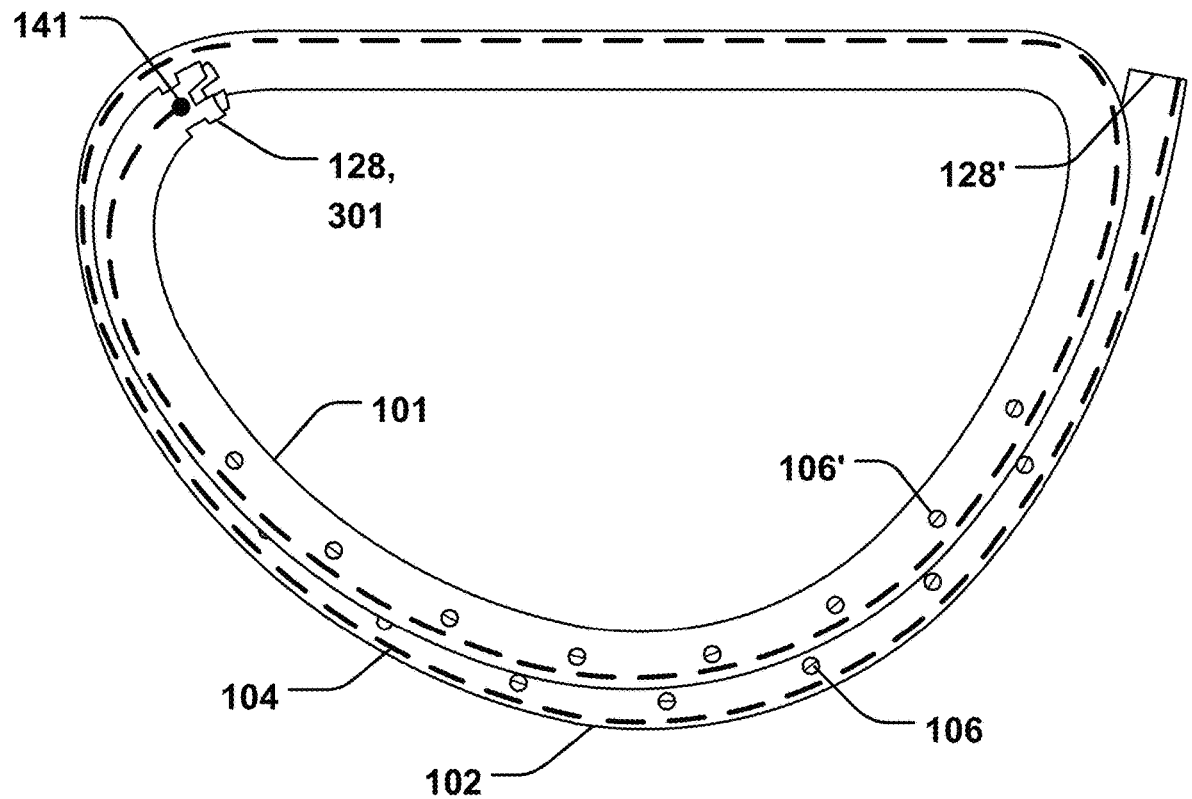
FIG. 16b is a schematic illustration of an annuloplasty device, in a top-down view, having oppositely arranged retention units and an interior stiffening unit.

The stiffening unit 104 may be attached to the first and/or second support ring 101, 102. The stiffening unit 104 may be attached to the first and/or second support ring 101, 102, already before the annuloplasty device 100 is implanted. This may be advantageous in applications where an increased stiffness of the annuloplasty device 100 is desired already before it is inserted into the body. FIG. 16b is a schematic illustration showing an annuloplasty device 100 having an attached stiffening unit 104. In this example the stiffening unit 104 extends between the free ends 128, 128'. The stiffening unit 104 may be made from NiTinol, and have the corresponding coil-shaped form as the first and second support rings 101, 102. Although not illustrated in FIG. 16b having the stiffening unit 104 attached to the first and/or second support ring 101, 102, in combination with having slits 135 or a spirally cut tubular material 109 provides for a particularly advantageous combination of having readily bendable first and second support ring 101, 102, due to the slits 135 or spirally cut material 109, as well as an increased strength provided by the attached stiffening unit 104. The stiffening unit 104 may provide for avoiding material fatigue while still having the advantageous bendable properties of the support rings 101, 102. The annuloplasty device 100 may thus provide for conforming to the anatomy and following the motion of the heart, as well as for mechanical properties that sustain the desired function over an increased time span.

The stiffening unit 104 may be attached to only one fixation point 141 along the first or second support rings 101, 102, e.g. by welding or other adhesion mechanisms. This provides for optimizing the ability to allow a certain relative motion between the stiffening unit 104 and first or second support rings 101, 102, as the latter is bent during implantation or subjected to movement when being implanted. Hence, the mechanical properties of the annuloplasty device 100 are improved for various stages of its manipulation. The fixation point 141 may be at one of the free ends 128, 128'. FIG. 16b shows the fixation point 141 at a proximal free end 128 where a connector 301 is arranged. Having the fixation point 141 at the proximal end 128 may be particularly effective for optimizing the advantageous properties as described above.

Figure 16C:
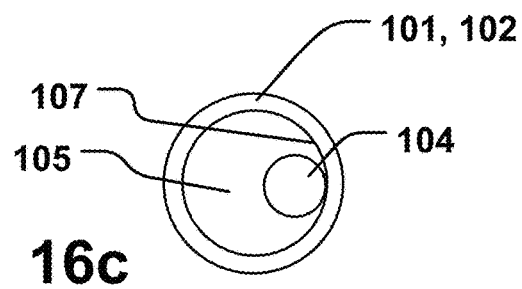
FIG. 16c is a schematic illustration of an annuloplasty device, in a cross-sectional view, having an interior stiffening unit.

The stiffening unit 104 may be fixed to a circumferential wall 107 enclosing the interior channel 105, as schematically illustrated in FIG. 16c. Having the stiffening unit 104 fixed to the wall 107 may facilitate bending of the first and/or second support rings 101, 102, in some directions. For example, in case the circumferential wall 107 have slits 135 at a position opposite the stiffening unit 104, the slits 135 may be able to accommodate a greater range of movement when the distance between the slits 135 and the stiffening unit 104 is maximized. In case the stiffening unit 104 is attached at only one fixation point 141, e.g. at the proximal 128 or distal 128' free end, the stiffening unit 104 may move freely in the interior channel 105 and conform to the shape of least resistance. The diameter of the stiffening unit 104 may be suitable to allow the simultaneous passage of guide wire 114 in the interior channel 105, thus providing for a facilitated positioning of the first and second support rings 101, 102, as described further below.

Figure 6A:
FIG. 6a is a schematic illustration of portions of the support rings of an annuloplasty device having expanded retention units, according to an example.
Figure 6B:
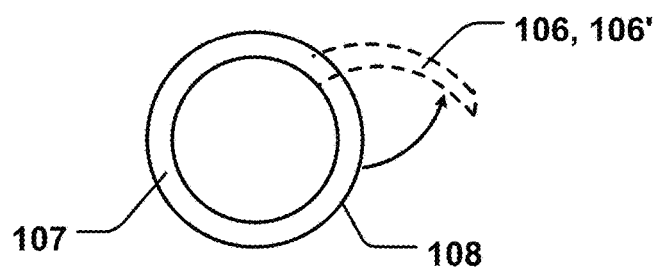
FIG. 6b is a schematic illustration, in a cross-sectional view of FIG. 6a, of a support ring of an annuloplasty device having expanded retention units, according to an example.
Figure 6C:
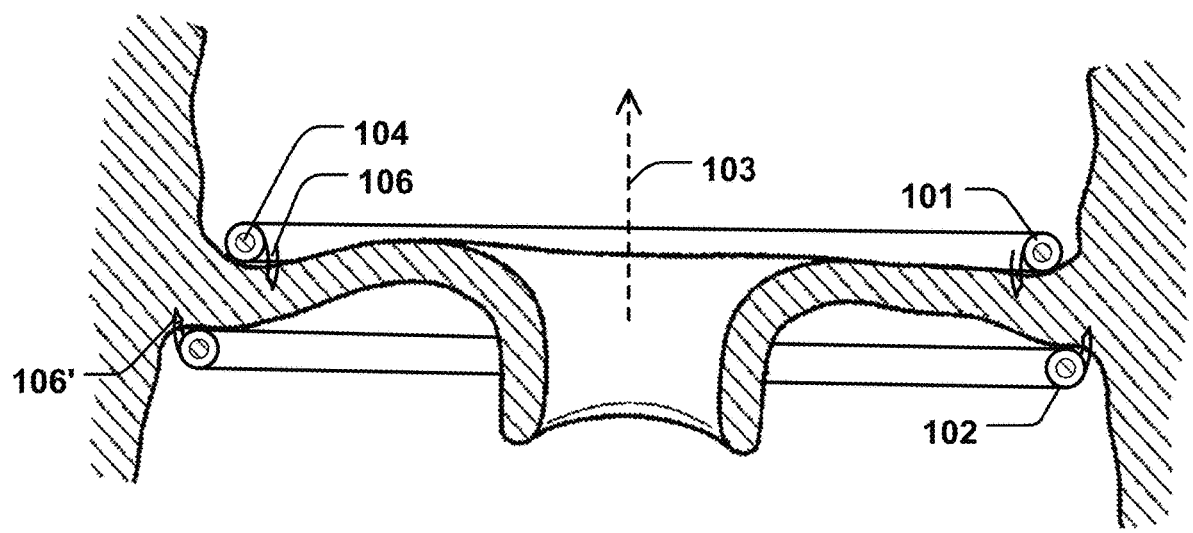
FIG. 6c is a schematic illustration of first and second support rings of an annuloplasty device arranged in a coiled configuration on opposite sides of heart valve leaflets, and expanded retention units engaged into valve tissue, according to an example.
Figure 7A:
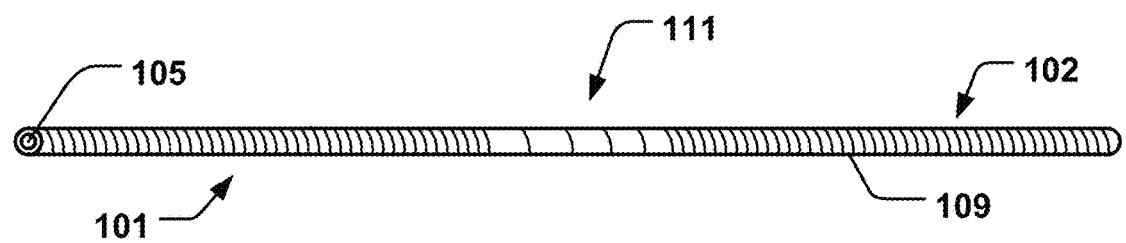
FIG. 7a is a schematic perspective view of an annuloplasty device, according to an example.
Figure 10A:
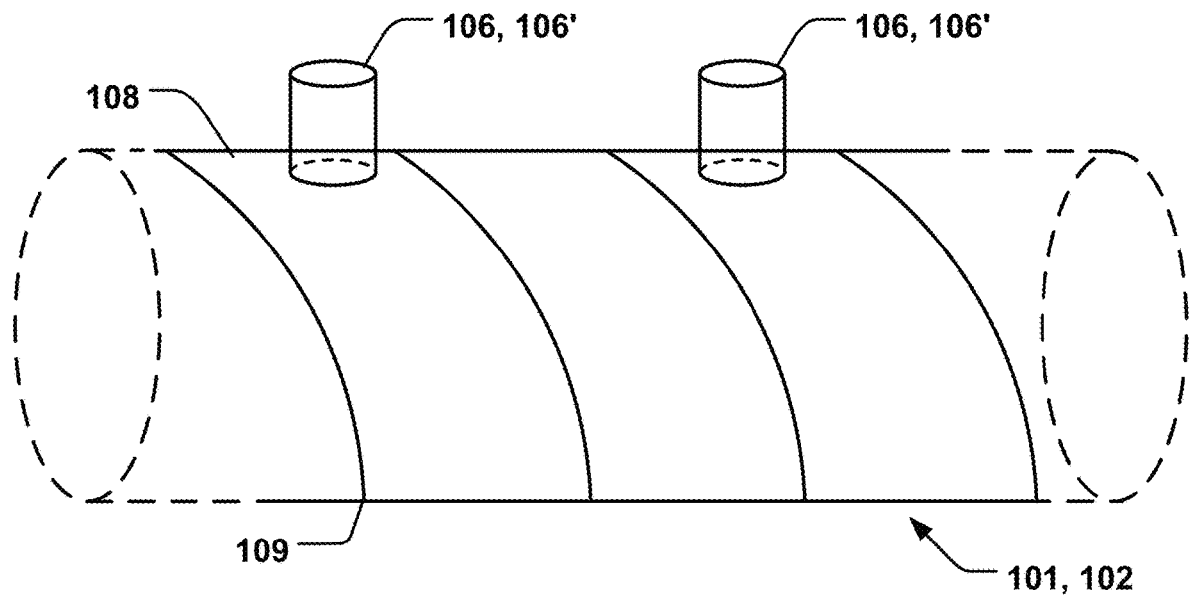
FIG. 10a is a schematic illustration, in a perspective view, of a support ring of an annuloplasty device having retention units, according to an example.
Figures 10B, 10C:
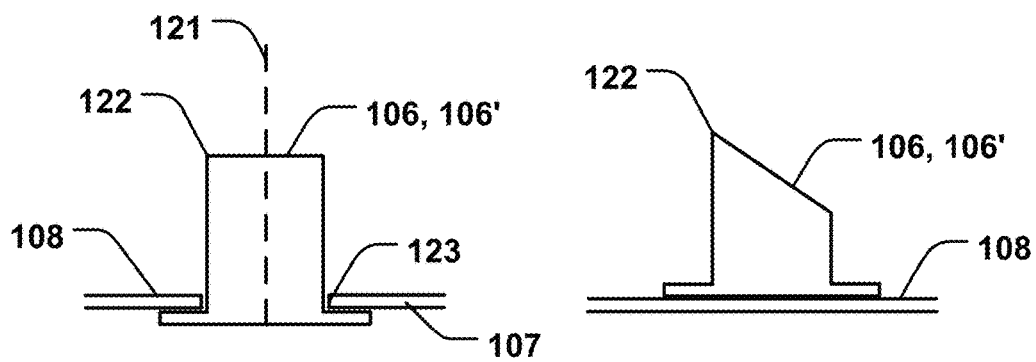
FIGS. 10b-d are schematic illustrations, in cross-sectional side views, of a support ring of an annuloplasty device having retention units, according to an example.

The annuloplasty device 100 may comprise retention units 106, 106', integrated with the first and/or second support rings 101, 102. FIG. 6a shows an example of elongate sections of the first and second support rings 101, 102, having respective retention units 106, 106'. FIGS. 10a-c show further examples of retention units 106, 106', as will be described further below. FIG. 6*b* show an example, in a cross-sectional view of FIG. 6*a* (i.e. looking along the longitudinal direction in which the first and second rings 101, 102, extend) where the retention units 106, 106', extend from the first and/or second support rings 101, 102. FIG. 6*c* show an example where the retention units 106, 106', engage into valve tissue from the opposite sides of the heart valve. Although FIG. 6*c* show retention units 106, 106', in the form illustrated in the example of FIGS. 6*a-b* it should be understood that the retention units 106, 106', may have other forms, such as illustrated in FIGS. 10*a-c*. This provides for an effective retention and fixation of the first and second rings 101, 102, in relation to the valve 301. It should be understood that in one example only the first or second support ring 101, 102, may comprise retention units 106, 106'. FIG. 7*d*, which will be described further below, is a further illustration showing retention units 106, 016', in a stretched elongated state of the annuloplasty device 100.

By having retention units 106, 106', integrated with the first and/or second rings 101, 102, a robust, less complex and more readily implementable fixation mechanism can be provided. As illustrated in e.g. FIG. 6*a*, a plurality of retention units 106, 106', may be provided on the respective first and second supports 101, 102. Each individual retention unit 106, 106' may engage or pierce into the tissue with a short distance, for a minimum amount of injury to the tissue. The sum of the retention force and friction created from all the retention units 106, 106', still provides for a strong fixation into the tissue. The scar healing will be quick since each individual retention unit 106, 106', as relatively small dimensions. This provides for a non-traumatic and still secure fixation of the annuloplasty device 100. Hence, the retention units 106, 106', provides for tissue fixation at multiple points across the annuloplasty device 100 instead of a few, e.g. 5 or 7 isolated stiches, resulting in reduced forces per fixation point, and no need for bulky stitching device or knotting device. There is further no risk of coronary artery occlusion or coronary sinus perforation. Hence, the annuloplasty device 100 provides for ease of operation, and a less time consuming procedure than stitching.

Figure 2A:
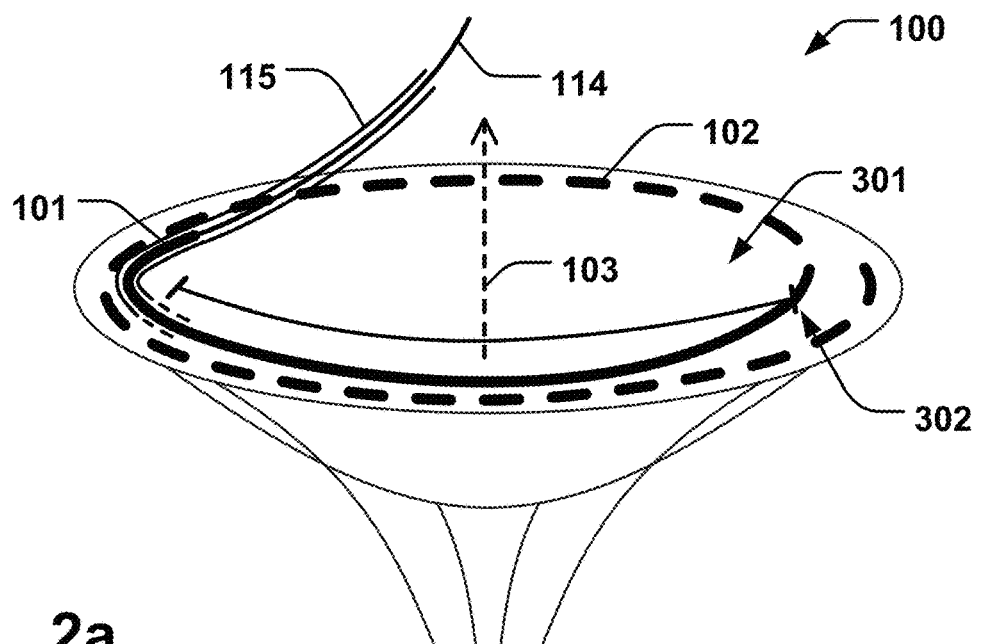
FIGS. 2a and 2c are schematic illustrations of first and second support rings of an annuloplasty device and a surrounding sheath arranged over a guide wire and in a coiled configuration on opposite sides of heart valve leaflets, according to an example.
Figure 2B:
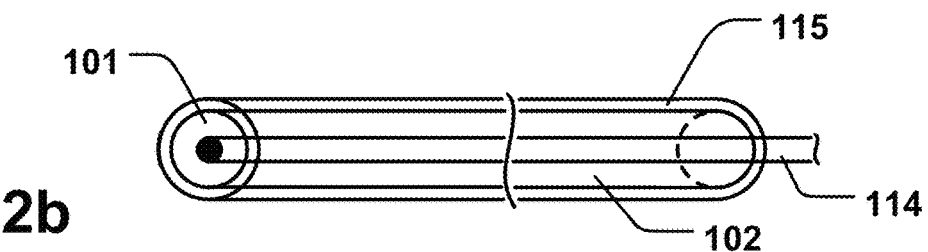
FIG. 2b is a schematic illustration, in a side-view section, of support rings of an annuloplasty device arranged inside a sheath and over a guide wire, according to an example.
Figure 2C:
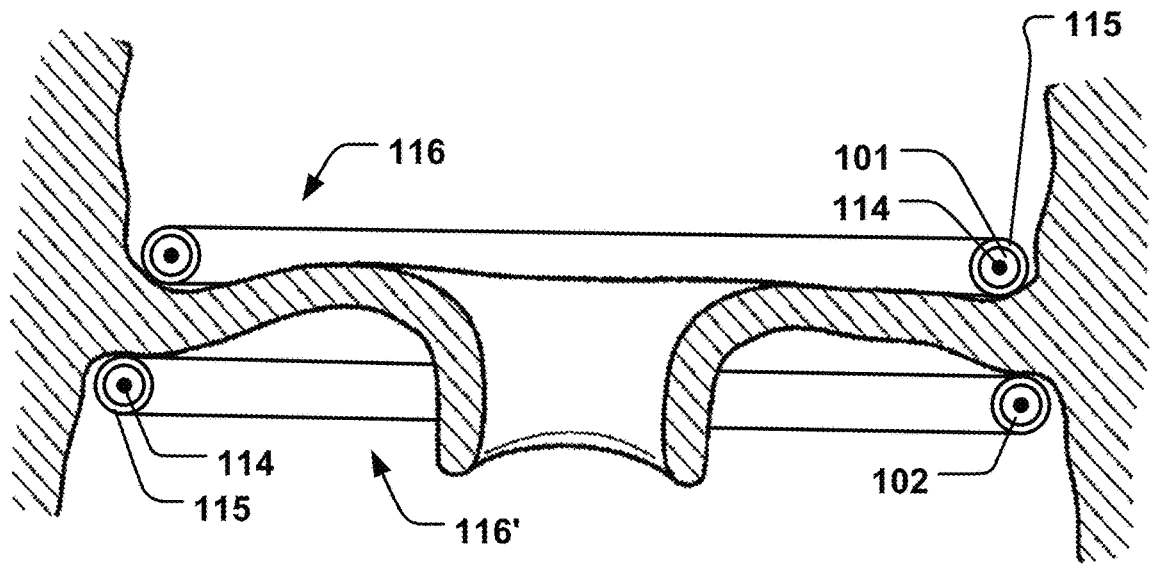
Figure 2D:
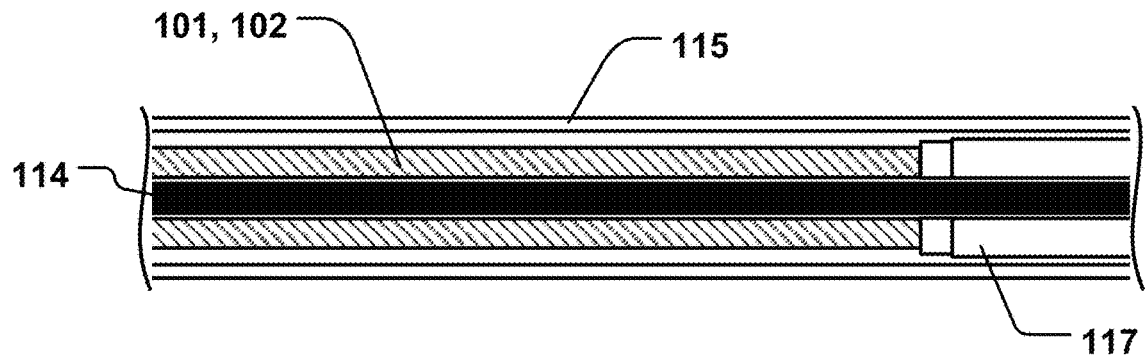
FIG. 2d is a schematic illustration, in a detailed side-view section, of a portion of a support ring of an annuloplasty device connected to a delivery device and arranged inside a sheath and over a guide wire, according to an example.
Figure 2E:
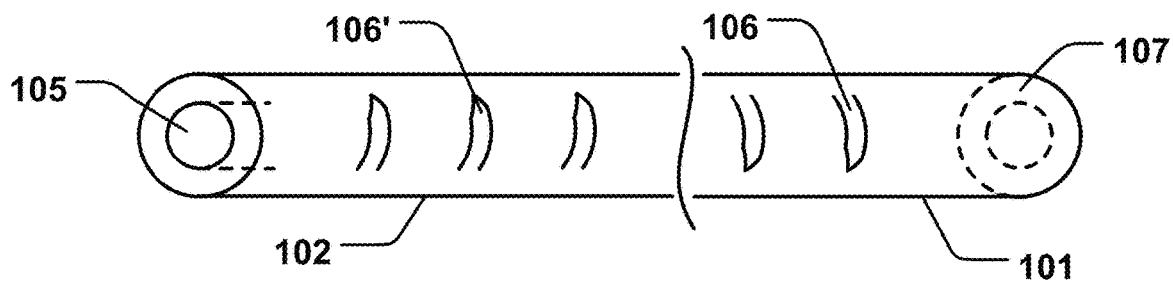
FIG. 2e is a schematic illustration of portions of the support rings of an annuloplasty device having retracted retention units, according to an example.
Figure 2F:
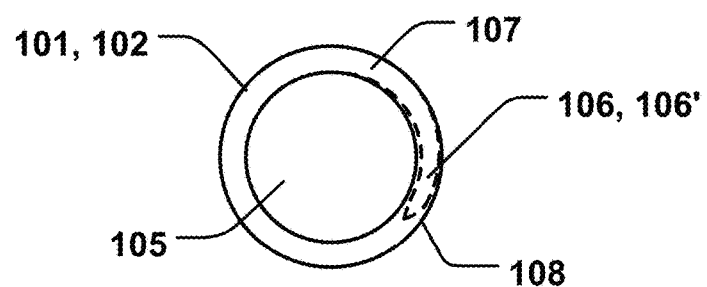
FIG. 2f is a schematic illustration, in a cross-sectional view of FIG. 2e, of a support ring of an annuloplasty device having retracted retention units, according to an example.

The first and/or second support rings 101, 102, may be formed from a material into a tubular shape with circumferential walls 107 enclosing said interior channel 105, as schematically illustrated in e.g. FIGS. 2*e-f* and 6*b*. The retention units 106, 106', may be formed from the material of the circumferential walls 107. This may provide for particularly robust and strong retention units 106. The retention units 106 may be formed from the material of the first support 101. Similarly, retention units 106' may be formed from the material of the second support 102. The retention units 106, 106', may be cut into shape from the material of the circumferential walls 107. The first and second supports 101, 102, may be integrated and formed from a continuous piece of material. Hence, the retention units 106, 106', may also be formed from such material.

Figure 10D:
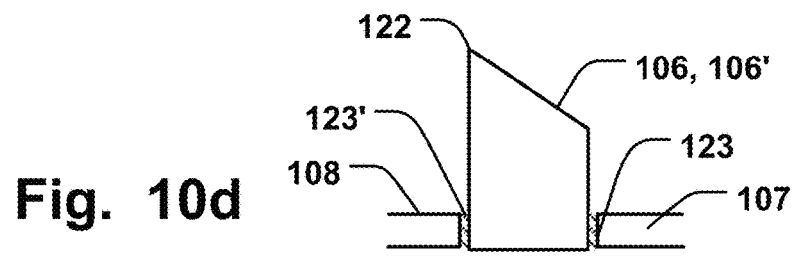
Figure 10E:
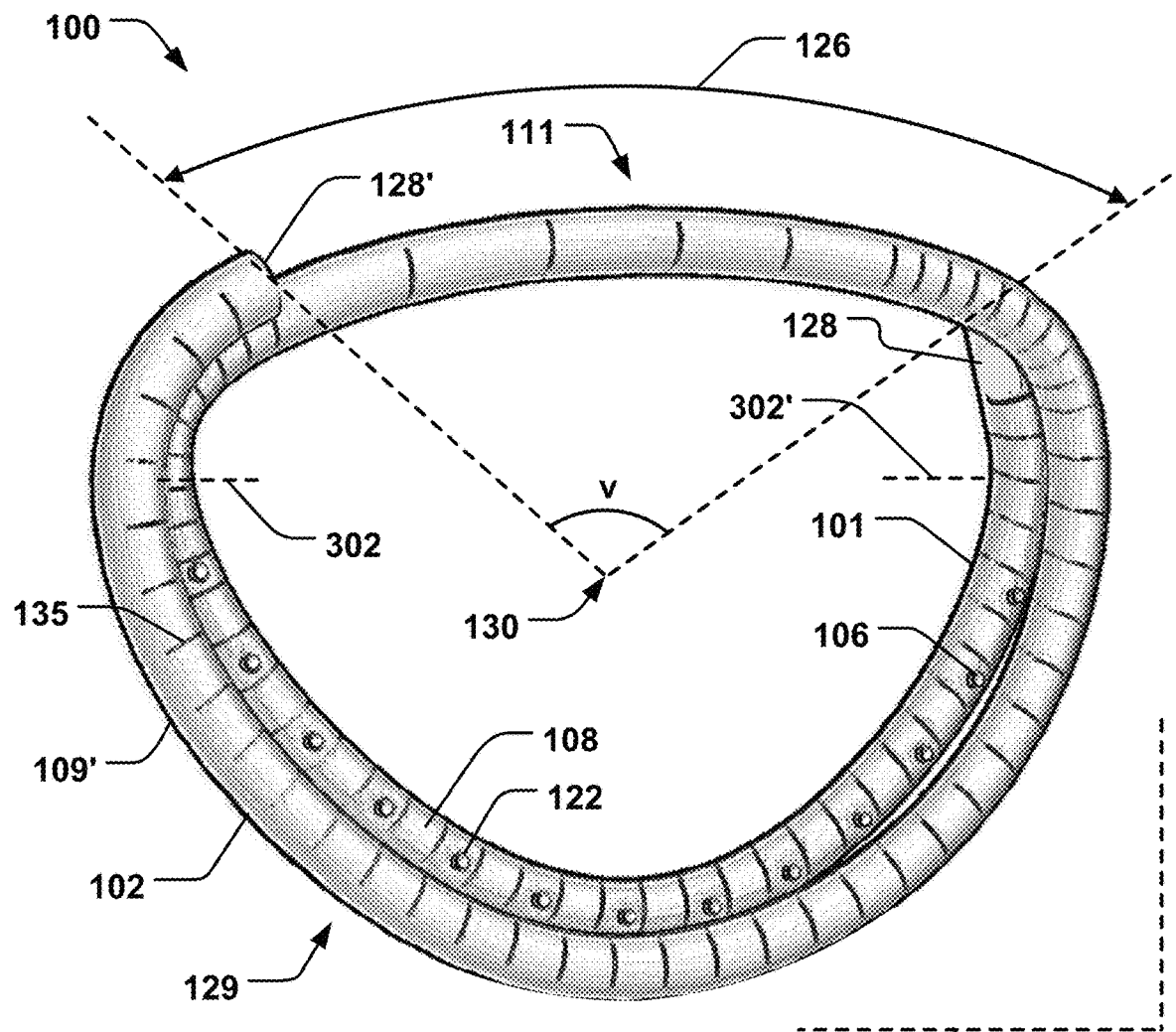
FIGS. 10e-f are schematic illustrations of an annuloplasty device having retention units, and off-set free ends, according to an example.

The retention units 106, 106', may be cut to form various shapes for optimizing the gripping force into the tissue. The retention units 106, 106', may be formed by different cutting techniques such as milling or laser cutting techniques. It is also conceivable that the retention units 106, 106', are fixed or integrated onto the respective support rings 101, 102, by other methods, or by being formed from other materials. For example, turning to FIGS. 10*a-c*, the retention units 106, 106', may be separate elements rigidly attached to the first and/or second supports 101, 102. FIG. 10*a* is a schematic perspective view of a section of the first support 101, or the second support 102. The retention units 106, 106', may be formed as elongated pins as shown in the examples of FIGS. 10*a-c*. In one example, the height of the retention units 106, 106', above the surface 108 is 0.2-1 mm. A particularly advantageous height of the retention units 106, 106', above the surface 108 may be 0.3 mm. The retention units 106, 106', may thus extend in a longitudinal direction 121 and may be cut with a right angle (FIG. 10*b*) or an acute angle (FIG. 10*c*) to the longitudinal direction 121 so that a sharp edge 122 is formed which can engage surrounding tissue. The retention units 106, 106', may be arranged at a determined interval. E.g. in case the first and/or second support rings 101, 102, are formed from a spirally cut tubular material 109 the retention units 106, 106' may be attached to every, or every other (as seen in the example of FIG. 10*a*) loop of the spirally cut tubular material 109. Also, the retention units 106, 106', may be arranged at a determined interval on the tubular material 109' having slits 135 as shown in the example of FIG. 10*e*, e.g. between every other pair of slits 135 as shown. The retention units 106, 106', shown in FIGS. 10*a-c* may be arranged as described in relation to FIG. 7*d*. FIG. 10*b* shows an example where the retention unit 106, 106', is arranged through an opening 123 in the circumferential wall 107 of the first and/or second support 101, 102. FIG. 10*c* show an example where the retention unit 106, 106', is attached to the surface 108 of the first and/or second support 101, 102. In both cases, the retention unit 106, 106', may be fixed by welding, by an adhesive or by other fixation elements or materials. This provides for a particularly robust and strong configuration of the retention unit 106, 106', on the annuloplasty device 100. FIG. 10*d* show another example where the retention unit 106, 106', is arranged through an opening 123 in the circumferential wall 107 of the first and/or second support 101, 102, but without a flange as seen in FIG. 10*b*. This provides for facilitating manufacturing as the retention unit 106, 106', may be inserted from the outside into the opening 123, and attached by e.g. a weld 123' to the wall 107.

Turning again to the example of FIGS. 6*a-b*, the retention units 106, 106', may comprise a shape-memory material. Such shape memory material may be the same material from which the first and/or second supports are formed, as discussed above. Activation of the shape-memory material may cause the retention units 106, 106', to transfer from a retracted state, in which the retention units 106, 106', are flush with an outer surface 108 of the first and/or second support rings 101, 102, as illustrated in the examples of FIGS. 2*e-f*, to an expanded state, in which the retention units 106, 106', protrudes form the outer surface 108 of the first and/or second support rings 101, 102, as illustrated in the examples of FIGS. 6*a-b*. This provides for facilitated positioning of the first and second support rings 101, 102, while the retention units 106, 106', are retracted, while an efficient fixation is attained in the implanted state of the rings 101, 102, when the retention units 106, 106', are expanded.

The shape-memory material may be configured to assume the expanded state of the retention units 106, 106', in response to an activation temperature. For example, the temperature may be increased to an activation temperature, so that the retention units 106, 106', assume the expanded state. It is conceivable that the annuloplasty device 100 and the retention units 106, 106', thereof may be kept at a defined temperature while arranged in a delivery catheter. Subsequently, when the device 100 is exposed to the warm tissue, the activation temperature may be reached, so that the retention units 106, 106', can be forced into the tissue. In one example the first and second support rings 101, 102, may be formed from a shape-memory material that may cause a decrease of the pitch distance ($p_1$, $p_2$), as discussed above, in response to an activation temperature. A synergetic effect for fixation of the annuloplasty device 100 may thus be utilized as the rings 101, 102, contract to pinch the valve tissue and the retention units 106, 106', expand to engage into the tissue. A further emphasized effect may be provided by the stiffening unit 104 which provides for increasing the rigidity of the rings 101, 102, as discussed above, so that retention units 106, 106', can engage the tissue with an enhanced retention force. The stiffening unit 104 may in addition push the rings 101, 102, towards each other from the opposite sides, as described above, to further add to the retention force of the rings 101, 102, against the tissue. A particularly efficient and secure implantation can thus be realized.

The first and/or second support rings 101, 102, may be formed from a spirally cut tubular material 109 enclosing the interior channel 105. FIG. 7a show a schematic example of such spirally cut tube, i.e. shown as the elongated form of the first and second rings 101, 102, when stretched apart, before assuming the coiled shape. The spirally cut material provides for an enhanced flexibility of the first and second support rings 101, 102. The length of the spirally cut portions of the tube 109 may vary to adapt the flexibility along the portions of the annuloplasty device 100 and thereby tailor the device 100 to various anatomies. In the example of FIG. 7a, a portion 111 corresponding to an anterior portion 111 (see e.g. FIG. 5a) of the device 100 when in the coiled shape, has been spirally cut with a greater separation between adjacent loops of the spirally cut material compared to the cuts in the remaining length of the first and second supports 101, 102. The rigidity of the anterior portion 111 may thus be increased so that the annuloplasty device 100 is less bent along this portion or assumes a substantially straight shape. Alternatively, portion 111 is not spirally cut at all. Having a few cuts may however improve the flexibility when delivering the annuloplasty device 100 through a catheter. The annuloplasty device 100 may thus assume a D-shape in a facilitated manner. Other shapes may be provided by varying the flexibility as described. The first and/or second support rings 101, 102, may be formed from a tubular material 109' enclosing the interior channel 105, where the tubular material 109 comprises slits 135 as schematically shown in e.g. FIGS. 10e, 17b, 18a-c, 19. The slits 135 extend around part of the circumference of the tubular material 109', and may arranged along at least part of the circumference facing the center point 130, as shown in FIG. 10e. This may provide for facilitating the first and second supports 101, 102, to bend as desired and assume the coiled shape. The slits 135 may extend substantially perpendicular to the axial direction (A) along which the first and second supports 101, 102, extend, i.e. along direction N' as illustrated in e.g. FIG. 17b. As with the spirally cut tubular material 109 described above, the distance between adjacent slits 135 may be varied along the length of the first and second supports 101, 102. E.g. The anterior portion 111 may have longer such distances compared to the posterior bows 110, 110'.

Figure 19:
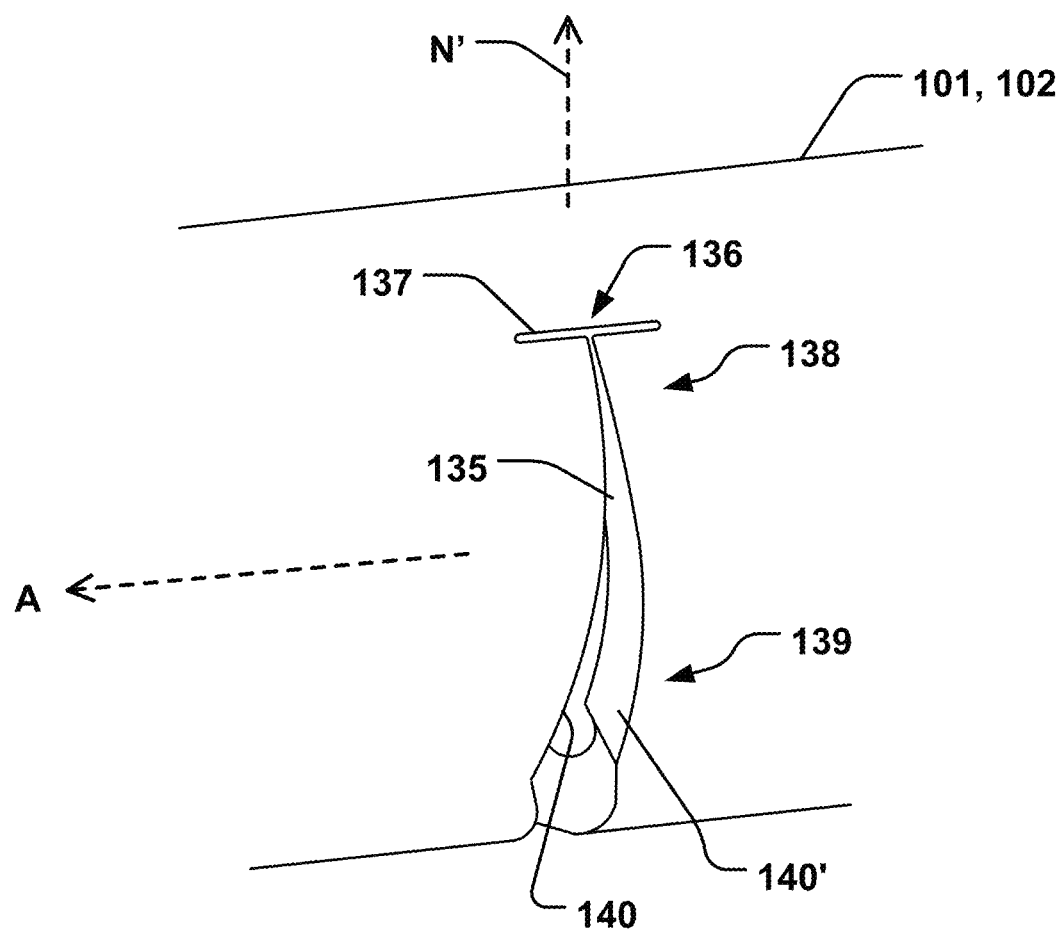
FIG. 19 is a schematic illustration of a further detailed perspective view of a slit in a section of an annuloplasty device.

The slits 135 may extend from respective apex points 136 in the tubular material 109', i.e. the corner of the recess or opening formed by the slit 135, as indicated in FIG. 19. The slits 135 may comprise respective secondary cuts 137 extending through the respective apex point 136 in the axial direction (A), as further illustrated in FIG. 19. Having a secondary cut 137 or slot extending in a transverse direction to the main slit 135, at its corner or apex 136, provides for minimizing stress in the material at such corner or apex 136. This provides for reducing the risk of fatigue or breakage of the tubular material 109', since the tension in the material may be distributed along a wider area around the secondary cuts 137.

The slits 135 may taper from a narrow portion 138 towards a gap 139 as illustrated in the example of FIG. 19. The slits 135 may thus be wedge shaped in a direction (N') substantially perpendicular to the axial direction (A). The gap 139 may accommodate relative movement between opposite walls 140, 140', of the first and/or second support rings 101, 102, in said gap 139 along the axial direction (A), upon a bending motion of the first and/or second support rings 101, 102. I.e. as the first and/or second support rings 101, 102 bend, the first surface 140 may move closer to the second surface 140' in the gap 139. This provides for facilitating bending of the first and/or second support rings 101, 102. The angle of the wedge-shaped slit 135, formed between the opposite walls 140, 140', may be varied to control the desired radius of curvature by which the first and/or second support rings 101, 102, should bend. This angle may vary along the length of the first and/or second support rings 101, 102, to control the amount of bending at various sections thereof. E.g. the aforementioned angle or dimensions of the gap 139 may be adapted to accommodate a larger motion and thereby a greater amount of bending of the first and/or second supports 101, 102. This may be advantageous for example at either side of the anterior portion 111 of the annuloplasty device 100, i.e. at the corners with the smallest radius of curvature, see e.g. FIG. 10e. FIGS. 18b-c are also schematic illustrations showing how the gap 139 of the slit 135 reduce in width as the opposite walls 140, 140', of the gap 139 move closer to each other when bending the first and/or second support ring 101, 102, as shown in FIG. 18c.

The slits 135 may be curved so that the opposite walls 140, 140', of the first and/or second support rings 101, 102, extend with a convex or concave shape towards the axial direction (A), as further illustrated in the example of FIGS. 18b-c. Having a convex or concave shape of the opposite walls 140, 140', provides for increased stability in directions transverse to the axial direction (A) as the curved shape of the first wall 140 may be received in the correspondingly mating curved shape of the second wall 140', thereby reducing the risk of relative movement or dislocation in such transverse direction, e.g. perpendicular to the axial direction (A). FIG. 18a show a larger section of the first and/or second support ring 101, 102, where a plurality of slits 135 have such curved shapes.

The first and/or second support rings 101, 102, may comprise a plurality of slits 135 having a varying length (d) in a direction (N') perpendicular to the axial direction (A), as schematically illustrated in FIG. 17b. Having a varying length (d) of the slits 135 provides for a more efficient distribution of stresses in the tubular material 109' and reducing the risk of fatigue or breakage thereof. The slits 135 may be varied to follow a curvature 142 which is non-parallel or forms an angle with the axial direction (A), as illustrated in FIG. 17b.

Further, the first support ring 100 may be adapted to be arranged on an atrial side of the heart valve, and the second support ring 102 may be adapted to be arranged on a ventricular side of the heart valve, as illustrated in e.g. FIG. 5d. The first support ring 101 may comprise a first posterior bow 110 and the second support 102 may comprise a second posterior bow 110'. The first and second posterior bows 110, 110', may be adapted to conform to a posterior aspect of the heart valve, and the first and second posterior bows may be separated by the intermediate anterior portion 111. The anterior portion 111 may comprise a smooth surface, and the first and second posterior bows 110, 110', may comprise the spirally cut tubular material enclosing the interior channel 105. Having a smooth surface at the anterior portion reduces the risk of complications from damaging the tissue at this sensitive region of the valve. A smooth surface may be provided by having few or no spirally formed cuts as described above. Also, the retention units 106, 106', may be arranged on respective first and second posterior bows 110, 110', as illustrated in FIG. 7d (when the annuloplasty device 100 is in the elongated stretched state). This provides for avoiding piercing the tissue at an anterior portion 111, which can be associated with a greater risk of complications.

Hence, the first and second posterior bows 110, 110', may be separated by an intermediate anterior portion 111. First retention units 106 may be arranged with an off-set distance 113 from second retention units 106', as illustrated in FIG. 7d, so that the anterior portion 111 may comprise a smooth surface free from retention units 106, 106'. I.e. the first and second retention units 106, 106', may be arranged with an off-set distance 113 from the anterior portion 111 towards respective first and second posterior bows 110, 110'. The off-set distance 113 may be varied to optimize the annuloplasty device 100 to the particular anatomy while ensuring that there is no risk of piercing the tissue at the anterior side of the valve. The first support 101 may have the retention units 106 extending in a first direction, and the second support 102 may have the retention units 106' extending in an opposite direction.

Thus, the first support ring 101 may comprise first retention units 106, and the second support ring 102 may comprise second retention units 106'. The first and second retention units 106, 106', may extend from respective first and second retention portions 112, 112', to produce a retention force, in use, at both of said opposite sides, see FIG. 7d in conjunction with FIG. 5a. Having retention units 106, 106', at both sides of the valve provides for increasing the retention force and the strength by which the annuloplasty device 100 is fixated at the valve. The retention units 106, 106', engage the tissue from both of the mentioned sides, creating a strong retention force in the radial direction, i.e. perpendicular to the axial direction 103. The first and second supports 101, 102, pinch the tissue from both sides of the valve, so that the retention units 106, 106', a forced into the tissue. The retention units 106, 106', provides for shaping the annulus as desired even with a reduced pinching force, since the retention units 106, 106', provides for fixating the shape of the annulus in the radial direction because of the mentioned retention force. This provides for a more reliable implantation at the heart valve, both in the short term and in the long term.

The first and second retention units 106, 106', may extend in opposite directions along the axial direction 103, as illustrated in the example in e.g. FIG. 6c. I.e. the first and second retention units 106, 106', may extend from respective retention portions 112, 112', towards eachother, to clamp the tissue therebetween. It is conceivable however that the retention units 106, 106', may extend in different directions. The second retention units 106' may for example extend with an angle in a radially outward direction to engage tissue in a direction towards a tissue wall radially outside the annulus. FIG. 6c show only a few retention units 106, 106', for a more clear illustration, but it should be understood that a plurality of retention units 106, 106', may extend at a defined interval along the first and second support 101, 102, as shown in FIG. 7d and in FIGS. 9b and 10e when the device 100 has a coiled configuration.

Further, the position of the first retention units 106 may be off-set in the radial direction (perpendicular to the axial direction) with respect to the second retention units 106', as schematically illustrated in FIG. 6c. Thus, although both the first and second retention units 106, 106', may extend in the vertical direction, the risk of having the first retention units 106 to engage with the second retention units 106' is avoided, which otherwise may lead to fully penetrating the valve tissue. This may be realized by having different diameters of the support rings 101, 102, and/or by arranging the first and second retention units 106, 106', to extend from opposite sides (in the radial direction of FIG. 6c) of the respective support rings 101, 102. Furthermore, when the support rings 101, 102, are arranged in the coiled configuration, the first retention units 106 may be off-set with a distance 124 with respect to the second retention units 106', as schematically illustrated in FIG. 7e. This further minimizes the risk of having two opposite retention units 106, 106', contacting each other which could accordingly result in a complete penetration of the tissue.

The first retention units 106 may be arranged along at least a first retention portion 112 of the first support ring 101, and the second retention units 106' may be arranged along at least a second retention portion 112' of the second support ring 102. The first and second retention portions 112, 112', may be curved in the coiled configuration. Hence, the retention units 106, 106', may be arranged to extend along the curved shape of the coil- or helix shaped annuloplasty device 100. The first retention portion 112 may be configured to follow the curvature of the annulus of the heart valve, such as the mitral- or tricuspid valve. The second retention portion 112' may be configured to follow the shape of the valve from the ventricular side.

The annuloplasty device 100, i.e. annuloplasty implant 100, may comprise a shape memory material, such as NiTiNol, or another suitable biocompatible alloy that can be heat-set in defined shapes, in a heat treatment procedure. The shape-memory material may comprise a material having more than one phase, so that the shape of the support rings 101, 102, and the retention units 106, 106', may be actively varied as described above. The shape memory material can be conceived as any material that is able to change shape as desired, in response to outside interaction, for example with an energy source, such as providing heat and/or electromagnetic energy, that can be transferred to the implant to change its shape. It is also conceivable that the shape of the implant can be affected by direct mechanical manipulation of the curvature of the ring-shape of the implant 100, e.g. by transferring a force or torque to the implant 100 via a delivery device. Via the various mentioned shape-affecting procedures the implant 100 may assume an elongated delivery configuration for advancement in a catheter, an initial shape when positioned in a coiled configuration along the annulus of the valve, and also an activated shape such as the contracted state described above for enhancing the strength of the fixation at an annulus of the heart valve.

Figure 1B:
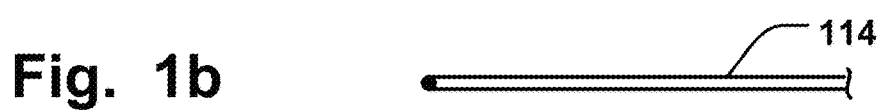
Figure 1C:
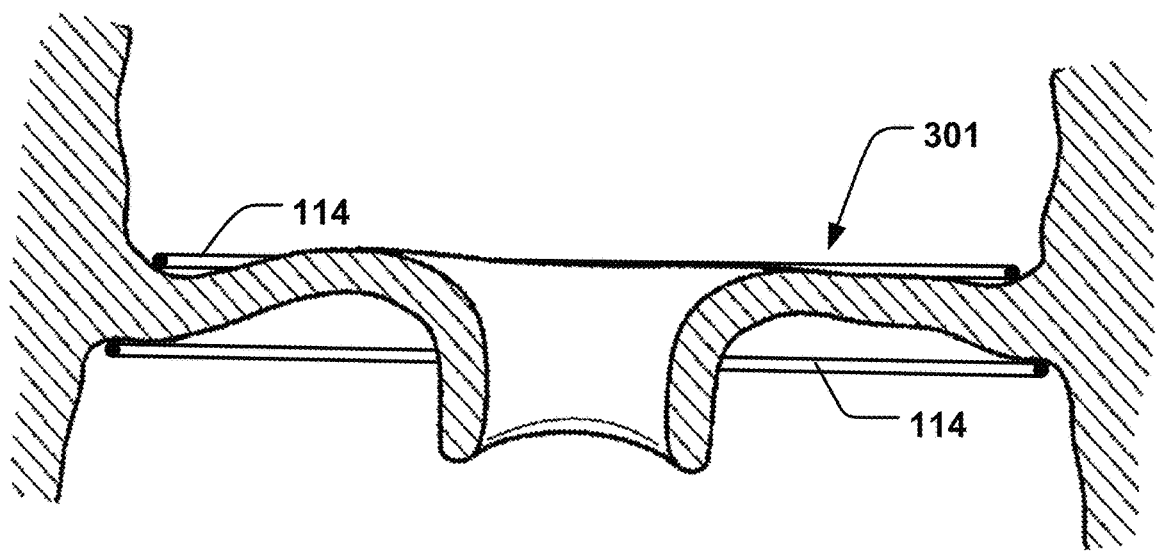
Figure 7B:
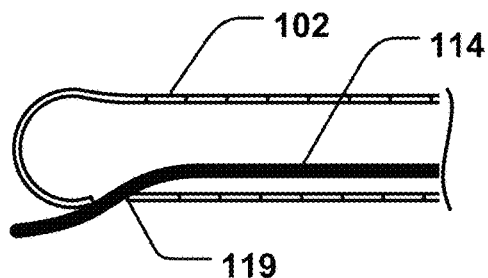
FIGS. 7b-c and 7f-i are schematic illustrations, in side view sections, of a distal portion of a support ring of an annuloplasty device, according to an example.
Figure 7C:
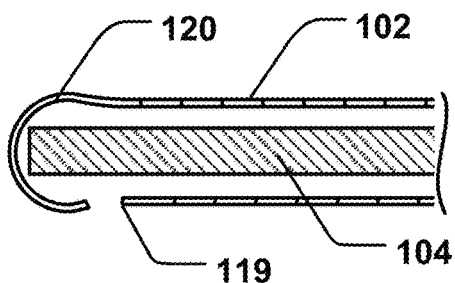
Figure 7D:
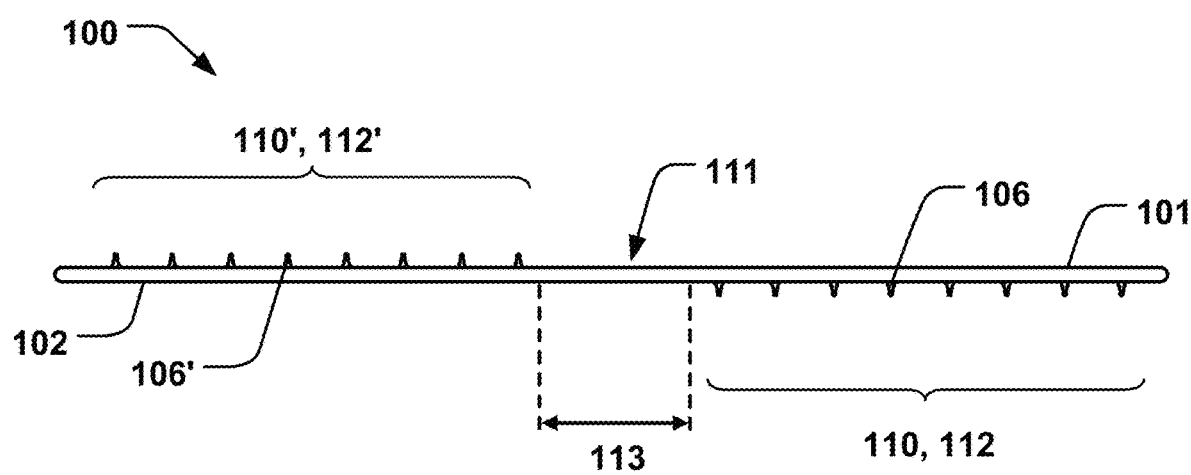
FIG. 7d is a schematic perspective view of an annuloplasty device, according to an example.
Figure 7E:
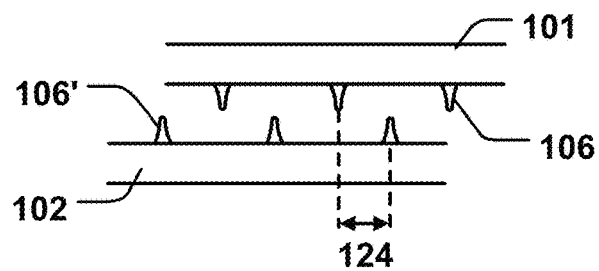
FIG. 7e is a schematic detail in a side view of an annuloplasty device, according to an example.
Figure 7F:
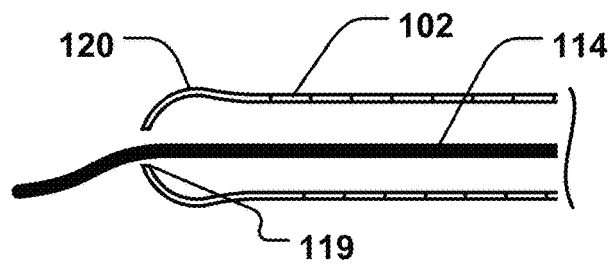
Figure 7G:
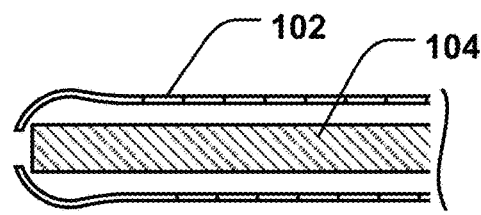
Figure 7H:
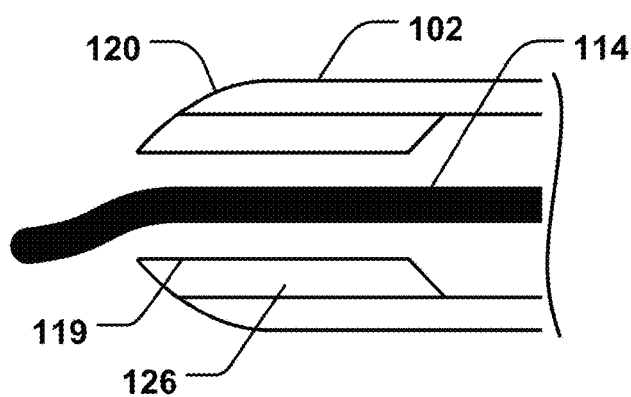
Figure 7I:
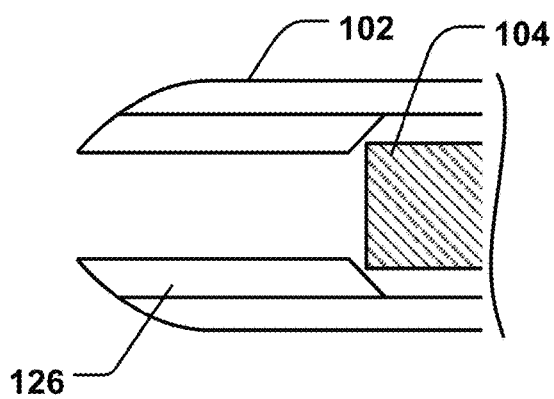

FIGS. 7b-c and 7f-i are schematic illustrations, in side view sections, of a distal portion of a support ring, such as the second support ring 102, of the annuloplasty device 100. The support ring 102 may comprise an opening 119 adjacent the distal end thereof, as exemplified in FIGS. 7b-c and 7f-i. The opening 119 may be sized so that a guide wire 114 may slide therethrough. Thus, the first and second support rings 101, 102, connected to form a tube 109, may be advanced over the guide wire 114. In this example, the guide wire 114 may pass along the interior channel 105, between opening 119 and a proximal opening (not shown) of the first support ring 101. The opening 109 adjacent the distal end of the second support ring 102 may be arranged in the side of the wall of the tube 109, as schematically illustrated in FIGS. 7b-c, or at a tip of the distal end, as schematically illustrated in FIGS. 7f-i. The distal end may be formed as an at least partly curved surface 120 which is curved to be atraumatic when pushed against the tissue. Having the opening 119 arranged through the side wall of the tube 109 allows for having the interior channel 105 of support ring 102 closed along the longitudinal direction in which the support ring 102 extends. The stiffening unit 104 may thus be inserted into the interior channel 105 until it abuts the closed distal end of the support ring 102, as schematically illustrated in FIG. 7c. Correct placement of the stiffening unit 105 may thus be facilitated after the guide wire 114 has been withdrawn. Alternatively, when having the opening 119 at the tip along the longitudinal direction of the support 102 as shown in FIGS. 7f-1, the opening 119 may have a smaller diameter than the stiffening unit 104, so that the latter can not pass through the opening 119 (FIGS. 7g and 7i). I.e. only the guide wire 114 may pass through opening 119 (FIGS. 7f and 7h). FIGS. 7h-l shown an example where a restriction element 126 at the distal end has an opening with a diameter which is less than the stiffening unit 104.

Figure 9B:
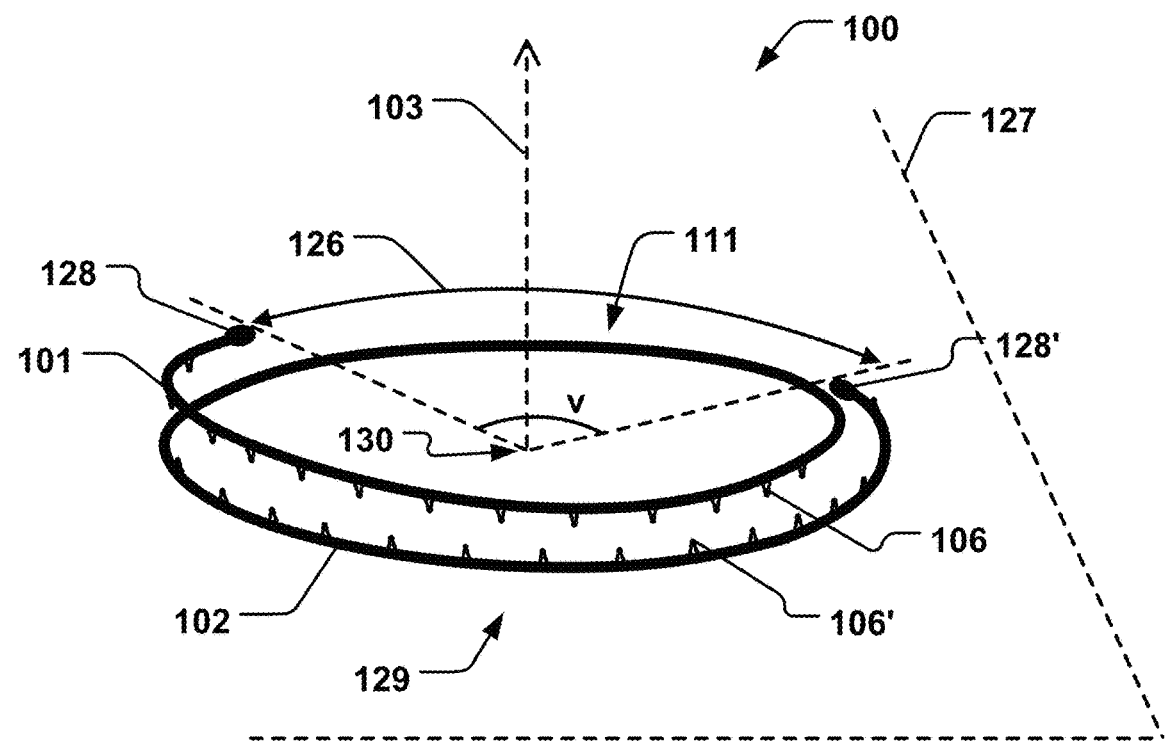
FIG. 9b is a schematic illustration, in a perspective view, of an annuloplasty device having retention units and off-set free ends, according to an example.
Figure 10F:
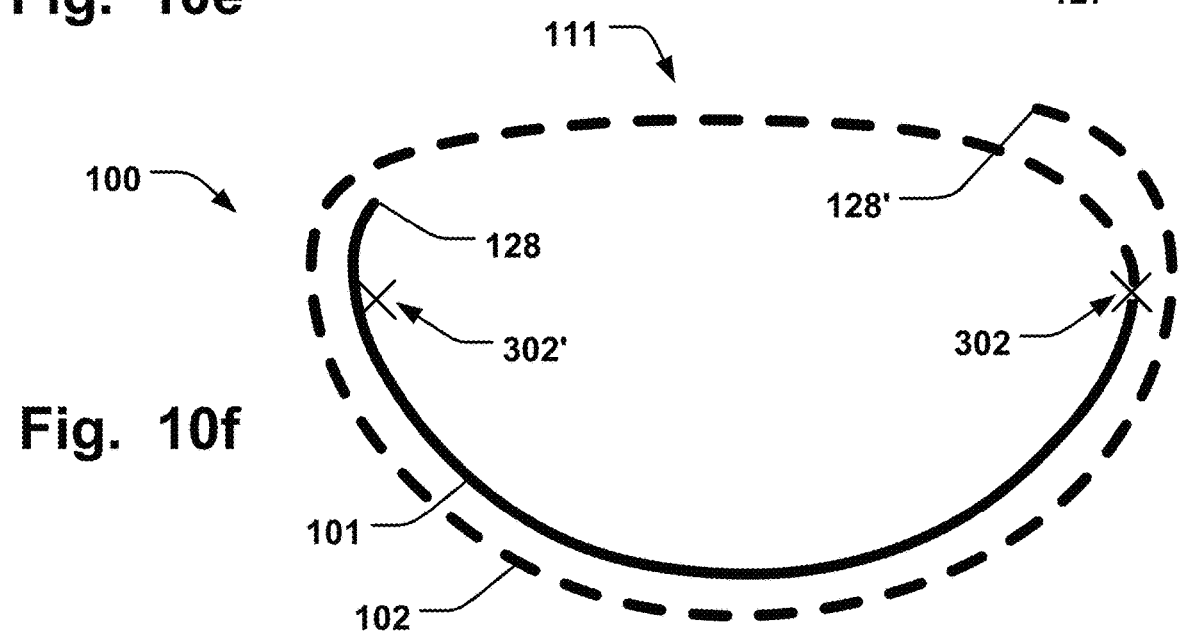

The first and second support rings 101, 102, may have respective free ends 128, 128', as illustrated in FIGS. 9b and 10e. The first and second support rings 101, 102, in FIGS. 9b and 10e may have an interior channel 105 configured to receive a stiffening unit 104 as described in relation to any of FIGS. 1-8. The free ends 128, 128', may be configured to be arranged on opposite sides of the native heart valve leaflets. The two free ends 128, 128', may be displaced from each other with a peripheral off-set distance 126 extending in a coil plane 127, as schematically illustrated in FIGS. 9b and 10e. The coil plane 127 is substantially parallel to an annular periphery 129 of the coil formed by the first and second support rings 101, 102, and perpendicular to the axial direction 103. The coil plane 127 accordingly corresponds to the plane spanned by the annular periphery 129 of the device 100 when assuming the coiled configuration. The peripheral off-set distance 126 between the two free ends 128, 128', thus extends substantially perpendicular to the central axis 103. This means that, when the device 100 is positioned in the implanted state, around the annulus of the heart valve, the two free ends 128, 128', will be separated along the plane of the valve. By having such off-set 126 in the plane of the valve, the resulting reduced length of the first or second support rings 101, 102, will allow for reducing the number of retention units 106, 106', required to securely fixate the device 100 at the valve, while at the same time providing for a sufficient overlap of the first and second support rings 101, 102, on the opposites sides of the valve to attain a sufficiently strong pinching effect therebetween to fixate the annulus in a modified shape. In situations, placing retention units 106, 106', on the anterior side may be associated with high risk. This can therefore be avoided, by having the off-set 126 as specified. Further, the anterior portion 111 may not be provided by retention units 106, 106', as has described above. Furthermore, the interference of the device 100 with the movements of the valve will be minimized when having an off-set 126. Fastening of the device 100 on the atrial side can thus be accomplished by fixation of the posterior bow 110, and there will be no interference on the atrial side with the movement of the valve, due to the off-set distance 126 reducing the circle sector of the first support 101. The coil of the first and second support rings 101, 102, may have a geometrical center point 130. The angle (v) between lines extending from respective free end 128, 128', and intersecting the center point 130, as illustrated in FIG. 9b, may be approximately 90 degrees. The angle (v) may be in a range 80-120 degrees to provide for the advantageous effects as described above. FIG. 10f show an example of how the first and second support rings 101, 102, and the free ends 128, 128', are placed relative commissures 302, 302'. The first support ring 101 may be positioned on the atrial side. The free end 128, which may connect to a delivery wire, may be arranged adjacent the anterior portion 111 or between the anterior portion 111 and the first commissure 302'. The first support ring 101 then extend past the first commissure 302' and follows the curvature of the annulus until extending through the second commissure 302, and continues to follow the valve on the ventricular side (dashed lines) as a second support ring 102. The second free end 128' may be arranged so that the second support ring 102 follows part of the shape of the anterior portion 111 of the first support ring 101, as exemplified in FIGS. 10e-f. The second free end 128' thus extends past the second commissure 302'. The two free ends 128, 128', may thus be separated with the off-set 126 along the anterior portion 111 of the implant 100. In the example of FIGS. 10e-f, the off-set distance 126 is less than the length of the anterior portion 111, since the first and second support 101, 102, are curved towards eachother at the first and second free ends 128, 128'. This may provide for an improved fixation of the implant 100 in some situations. However in some examples the off-set distance 126 may be increased to correspond substantially to the width of the implant along the anterior portion 111. The length of the off-set distance 126 may be between 50-100% of the length of the anterior portion 111 of the implant 100. The full length of the anterior side 111 may correspond substantially to the portion of the implant 100 that assumes a substantially straight extension, compared to the posterior bows 110, 110', or at least to the portion of the implant 100 that extends between the anterior and the posterior commissures 302, 302'.

The first retention units 106 and/or the second retention units 106' may extend in a longitudinal direction (L), and comprise a distal surface 118' forming a tapering shape towards a piercing edge 119', as schematically illustrated in the example of FIG. 11c. This provides for robust retention units 106, 106', allowing for effective grip into the surrounding tissue. The distal surface 118' may extend across the full width (w) of the retention unit 106, 106', so that the piercing edge 119' is positioned at the periphery of the width (w) as shown in the example of FIG. 11c. Alternatively, the retention units 106, 106', may be tapered towards a central piercing edge 119' as shown in the example of FIGS. 13a-b. In this case, the distal surface 118' may comprise two oppositely chamfered surfaces being joined along the centrally located piercing edge 119'. Alternatively, the retention units 106, 106', may comprise a conically tapering surface that narrows towards a centrally located piercing edge or tip 119' like a needle. Turning again to FIGS. 11a-c, the distal surface 118' extends in a plane having a normal axis (N) forming an acute angle (a) with the longitudinal direction (L). This provides for a robust retention unit 106, 106', while facilitating manufacturing thereof.

The first and second supports 101, 102, extend with an elongated shape along an axial direction (A), as schematically illustrated in e.g. FIG. 11b. The first and second supports 101, 102, are shown in the elongated stretched state, as in FIG. 7a, for a clearer presentation. The normal axis (N) may be substantially parallel with a plane spanned by the axial direction (A) and the longitudinal direction (L), as schematically illustrated in FIGS. 11*b-c*. This allows for arranging the piercing edge 119' so it extends transverse to the axial direction (A), and also transverse to a surrounding delivery catheter, when arranged therein, which may be advantageous in some applications when the implant 100 is delivered to the annulus. Any risk of wear or damage to the surrounding catheter may be reduced in such case.

The axial direction (A) is perpendicular to a radial direction (R) of the first and second supports 101, 102, as shown in FIGS. 12*a-b*. In this example, the normal axis (N) is substantially parallel with a plane spanned by the radial direction (R) and the longitudinal direction (L). This may provide for an enhanced grip in the surrounding tissue when the implant 100 is in the coiled shape around the annulus of the heart valve. The direction along which the piercing edge 119' extends may thus be aligned with the axial direction (A), which provides for an improved retention force into the tissue, as the tissue strive to move in a direction perpendicular to the axial direction (A) as the heart is beating, and when the implant 100 is in the coiled shape. The implant 100 may be coiled so that the radial direction (R) is directed from the center of the heart valve towards the annulus. In other situations, the implant 100 may be coiled so that the radial direction (R) is directed from the annulus to the center of the heart valve. As shown in the example of FIG. 12*a*, the shape of the second retention units 106' may be symmetric with the first retention units 106 with respect to the radial direction (R). It should be understood however that in some applications it may be advantageous to have respective vector components of the normal axis (N) along the radial direction (R) of the first and second retention units 106, 106', oppositely directed with respect to the radial direction (R).

The longitudinal direction (L) may extend with an angle (v), such as an acute angle (v), relative a normal axis (N') of a surface 120' of the first and/or second supports 101, 102, to which the first retention units 106 and/or the second retention units 106' are fixed, as schematically illustrated in FIG. 14*a*. Although the angle v is shown in the plane defined by the normal axis (N') and the radial direction (R) it should be understood that the retention units 106 may be angled in the plane defined by the normal axis (N') and the axial direction (A), i.e. having an angle v in the aforementioned plane. Having the retention units 106 angled in this direction may facilitate introduction of the implant 100 in a delivery catheter. Further, having angled retention units 106, 106', may provide for a further improved anchoring effect into the tissue and reduce the risk of dislocation between the retention units 106, 106', and the annulus. As in the previously described example, the implant 100 may be coiled so that the radial direction (R) is directed from the center of the heart valve towards the annulus. This may provide for further reducing the risk of having the annulus tissue to move relative the implant 100 in the radial direction (R) as the heart is beating. In other situations, the implant 100 may be coiled so that the radial direction (R) is directed from the annulus to the center of the heart valve. As shown in the example of FIG. 14*a*, the shape of the second retention units 106' may be symmetric with the first retention units 106 with respect to an axis of symmetry around the radial direction (R). It should be understood however that in some applications it may be advantageous to have respective vector components of the normal axis (N) along the radial direction (R) of the first and second retention units 106, 106', oppositely directed with respect to the radial direction (R).

The first retention units 106 and/or the second retention units 106' may be movable relative a normal axis (N') of surface 120' of the first and/or second supports 101, 102, to which the first retention units 106 and/or the second retention units 106' are fixed. The first retention units 106 and/or the second retention units 106' may be movable by being flexible. This provides for e.g. delivering the implant 100 in a more compact cross-sectional shape through a catheter, having the retention units 106, 106', deflected with a greater angle relative the normal axis (N'). Then, as the implant 100 is ejected from the catheter, the angle may be reduced so that the retention units 106, 106', extend a greater distance from the surface 120', for facilitated piercing into the tissue. The retention units 106, 106', may deflect with an angle (v) towards the radial direction (R) as shown in FIG. 14*a*, or with an angle (a) towards the axial direction (A) as shown in FIG. 11*b-c*. The first retention units 106 and/or the second retention units 106' may be movable by being formed by a shape memory material which changes shape over time, e.g. when being heated to an activation temperature.

The height (h) of the retention units 106, 106', may be in the range 0.5-2 mm, which may provide for a particularly advantageous grip into the tissue, while at the same time allowing for a facilitated delivery of the implant 100 from a delivery catheter to the annulus of the heart valve. The first and second retention units 106, 106', may be evenly separated along the length of the respective first and second supports 101, 102. The spacing between adjacent retention units 106, 106', may be in the range 0.5-2 mm. The spacing between adjacent retention units 106, 106', may also be in the range 1-1.5 mm, which may provide for a particularly advantageous anchoring into the tissue.

Any of the examples of annuloplasty devices 100 as exemplified in FIGS. 1-10 may comprise any of the retention units as describe in the examples of FIGS. 11-14.

The annuloplasty device 100 may comprise a delivery device connector 301 comprising a first locking structure 302 to interlock with a correspondingly mating locking structure 303 of a delivery device 117, as schematically illustrated in FIGS. 17*a-b*. The first locking structure 302 may comprise a first locking surface 302*a* to lock rotational movement of the annuloplasty device 100, when interlocked with the delivery device 117, around an axial direction (A) of the annuloplasty device 100. The first locking structure 302 may further comprise a second locking surface 302*b* to lock movement of the annuloplasty device 100 along the axial direction (A), when interlocked with the delivery device 117. Hence, both rotational movement around axis (A), and longitudinal movement along axis (A), may be effectively controlled by having such first and second locking surfaces 302*a*, 302*b*. This allows for a facilitated delivery and control of the position of the annuloplasty device 100. The first locking surface 302*a* may have a normal perpendicular to the axial direction (A), and the second locking surface 302*b* may have a normal parallel to the axial direction (A). FIG. 17*b* show one example of such locking structure 302.

Figure 17C:
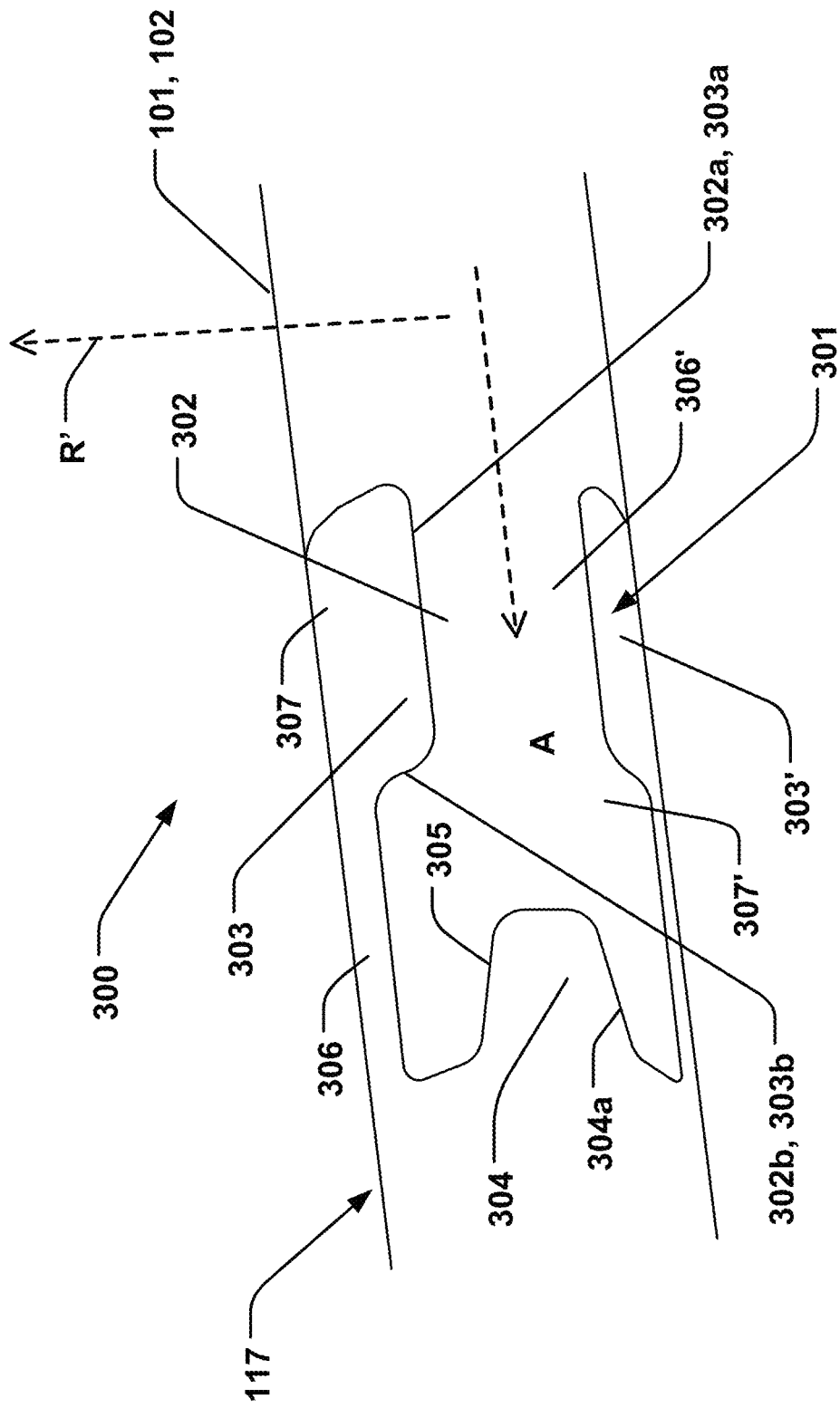
FIG. 17c is a schematic illustration in a further detailed perspective view of an annuloplasty device interlocked with a delivery device.

The first locking structure 302 may be substantially T-shaped to interlock with a correspondingly mating T-shaped locking structure 303 of a delivery device 117. The T-shaped first locking structure 302 may comprise a distal stem 306' being connected to a proximal tip 307' of increased width relative the distal stem 306, as schematically shown in the example of FIG. 17*c*. The proximal tip 307' may be configured to interlock with a proximal stem 306 of the delivery device 117. As further shown in the example of FIG. 17*c*, the distal stem 306' may be configured to interlock with a distal tip 307 of the delivery device 117. A robust and effective first interlocking structure 302 for interlocking with a delivery device 117 is thus provided. The annuloplasty device 100 may comprise two oppositely arranged T-shaped locking structures 302, although FIG. 17c only shows one locking structure for a clearer illustration. Having two such oppositely arranged locking structures 302, arranged to interlock with correspondingly mating locking structures 303 of a delivery device 100, also being oppositely arranged as described further below, provides for a particularly robust and effective connection interface between the annuloplasty device 100 and a delivery device 117.

The T-shaped first locking structure 302 may comprise a proximal recess 305 to receive a protrusion 304 of the delivery device 117. This provides for a self-centering positioning of the annuloplasty device 100 relative the delivery device 117 when the latter engages the first locking structure 302. The proximal recess 305 may be tapering in a direction from the delivery device 117 towards the first and/or second support rings 101, 102, as shown in the example of FIG. 17c. This provides for a protrusion 304 of the delivery device 117 to easier slide into the correct position in the recess 305.

A kit 300 comprising an annuloplasty device 100 as described above in relation to FIGS. 1-19 and a delivery device 117 is provided. The delivery device 117 comprises a locking structure 303 to interlock with a correspondingly mating first locking structure 302 of a delivery device connector 301 of the annuloplasty device 100. The locking structure 303 of the delivery device 117 comprises a first locking side 303a to lock rotational movement of the annuloplasty device 100, when interlocked with the delivery device 117, around an axial direction (A) of the annuloplasty device 100. The locking structure 303 of the delivery device 117 comprises a second locking side 303b to lock movement of the annuloplasty device 100 along the axial direction (A), when interlocked with the delivery device 117. An effective and robust connection mechanism between the delivery device 117 and the annuloplasty device 100 is provided.

A delivery device 117 for an annuloplasty device 100 is provided, comprising a locking structure 303 to interlock with a correspondingly mating first locking structure 302 of a delivery device connector 301 of the annuloplasty device 100. The locking structure 303 of the delivery device 117 comprises a first locking side 303a to lock rotational movement of the annuloplasty device 100, when interlocked with the delivery device 117, around an axial direction (A) of the annuloplasty device 100. The locking structure 303 of the delivery device 117 comprises a second locking side 303b to lock movement of the annuloplasty device 100 along the axial direction (A) when interlocked with the delivery device 117. A delivery device 117 providing for an effective control and positioning of an annuloplasty device 100 is thus provided.

The locking structure 303 may be movable from an interlocked state, when interlocked with the mating first locking structure 302 of the annuloplasty device 100, as shown in FIG. 17b, to a released state as shown in FIG. 17a upon which the locking structure 303 of the delivery device 117 deflects in a radial direction (R') thereof, perpendicular to a longitudinal direction (L') along which the delivery device 117 extends with an elongated shape. Hence, in the released state, the locking structure 303 of the delivery device 117 is released from interlocking engagement with the mating first locking structure 302 of the annuloplasty device 100. This provides for an effective and reliable interlocking and releasing of the annuloplasty device 100.

The delivery device 117 may comprise a sheath 305 being movable along the longitudinal direction (L'), as illustrated in FIG. 17a. The locking structure 303 may comprises a shape memory material being biased to deflect in the radial direction (R') to assume the aforementioned released state as illustrated in FIG. 17a. The sheath 305 is movable from an extended state in which the sheath 305 forces the locking structure to the interlocked state as shown in FIG. 17b (sheath 305 is omitted in FIG. 17b for a clearer illustration), to a retracted state as shown in FIG. 17a, in which the sheath 305 releases the restraining force on the locking structure 303 so that the locking structure 303 deflects in the radial direction (R') for releasing the annuloplasty device 100. This provides for an effective and reliable control of the interlocking and releasing of the annuloplasty device 100.

The locking structure 303 may comprise two oppositely arranged locking structures 303, 303', in the radial direction (R'). Thus, in said released state, the oppositely arranged locking structures 303, 303', may deflect in opposite radial directions, as schematically shown in the example of FIG. 17a.

The oppositely arranged locking structures 303, 303', may be symmetric in shape. This allows for interlocking with the annuloplasty device 100 when having the delivery device 117 in two different directions for a facilitated control.

The delivery device 117 may comprise a protrusion and/or recess 304 arranged between the oppositely arranged locking structures 303, 303', along the radial direction (R'), and extending in the longitudinal direction (L') to interlock with a correspondingly mating protrusion and/or recess 305 of the annuloplasty device 100. This provides for a facilitated centering of the annuloplasty device 100 relative the delivery device 117 as elucidated above.

The delivery device 117 may comprise a protrusion 304 as illustrated in FIG. 17b, and the protrusion 304 may taper towards the annuloplasty device 100, along the longitudinal direction (L'). Facilitated centering and interlocking of the annuloplasty device 100 may thus be provided as described above.

The locking structure 303 may be substantially T-shaped with a proximal stem 306 being connected to a distal tip 307 of increased width relative the stem 306, as illustrated in FIG. 17c. The distal tip 307 may be configured to interlock with a distal stem 306' of the annuloplasty device 100. Likewise, the proximal stem 306 may be configured to interlock with a proximal tip 307' of the annuloplasty device 100.

Figure 15A:
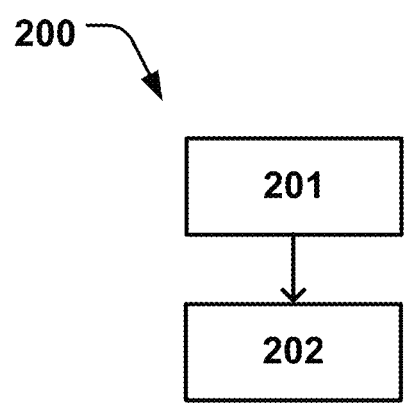
FIG. 15a is a flow chart of a method of repairing a defective heart valve according to one example.

A method 200 of repairing a defective heart valve is disclosed. The method 200 is schematically illustrated in FIG. 15a, in conjunction with FIGS. 1-6. The order in which the steps are described should not be construed as limiting, and it is conceivable that the order of the steps may be varied depending on the particular procedure. The method 200 comprises positioning 201 first and second support rings 101, 102, of an annuloplasty device 100 in a first configuration as a coil on opposite sides of native heart valve leaflets of the heart valve, as schematically illustrated in e.g. FIGS. 3a and 3d. The method 200 comprises increasing the stiffness of the first and/or second support rings 101, 102, by inserting 202 a stiffening unit 104 into an interior channel 105 arranged in at least part of the first and/or second support rings 101, 102, as schematically illustrated in FIGS. 4a-d, and FIGS. 5a-d. As discussed, the mentioned examples show the stiffening unit extending through both the first and second support rings 101, 102, length of the portion in the first and second support rings 101, 102, in which the stiffening unit 104 extends may be varied to change the rigidity of different sections of the annuloplasty device 100. Having a stiffening unit 104 arranged in the interior channel 105 provides for the advantageous benefits as discussed above in relation to the annuloplasty device 100 and FIGS. 1-10.

Figure 15B:
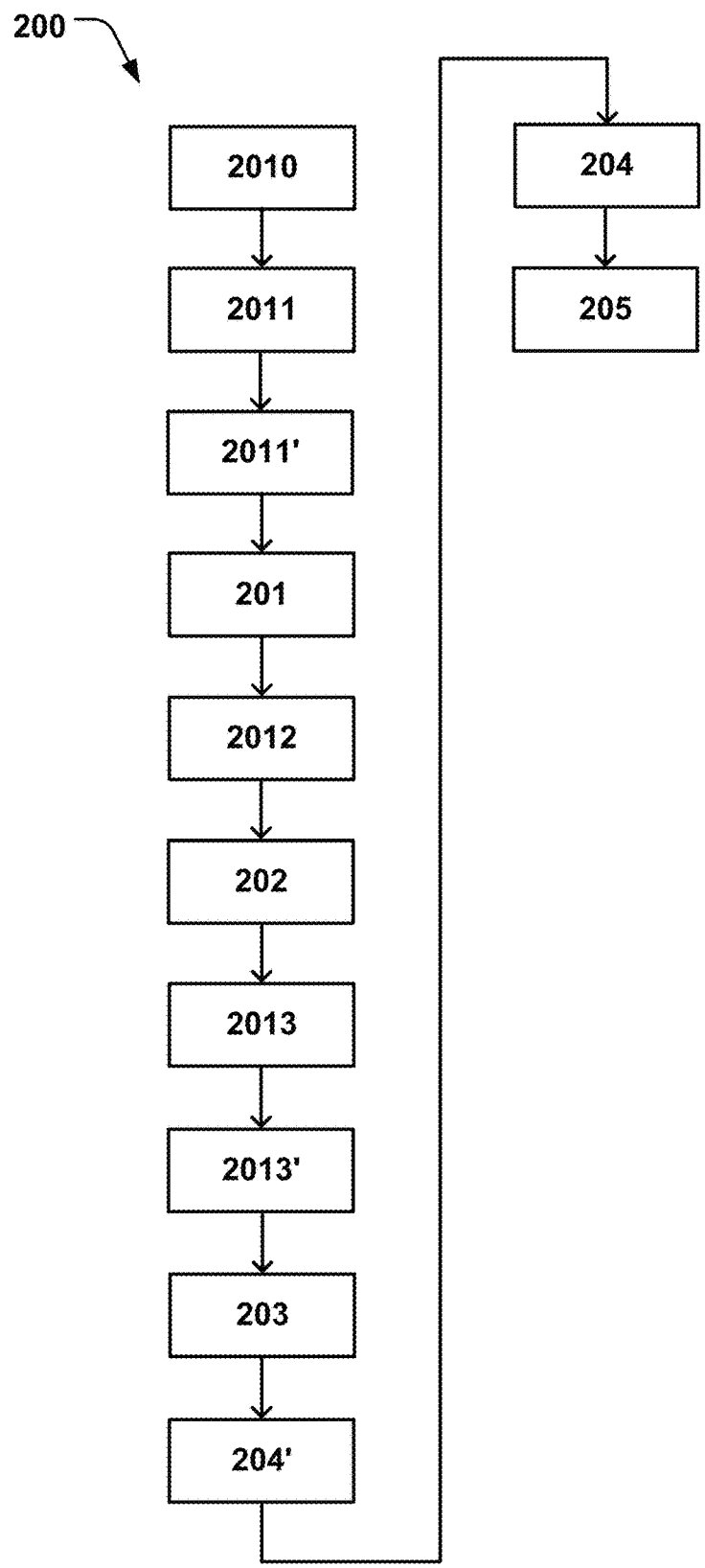
FIG. 15b is another flow chart of a method of repairing a defective heart valve according to one example.

A method 200 is schematically illustrated in FIG. 15b, in conjunction with FIGS. 1-6. The order in which the steps are described should not be construed as limiting, and it is conceivable that the order of the steps may be varied depending on the particular procedure. Positioning the first and second support rings 101, 102, may comprise advancing 2011 the first and second support rings 101, 102, over a guide wire 114 extending through the interior channel 105 to assume said coil on the opposite sides of the heart valve. FIGS. 1a and 1c show a guide wire 114 arranged as a coil at the opposite sides, extending through a valve commissure 302. The dashed line portion correspond to the portion of the guide wire 114 arranged on the ventricular side. The first and second support rings 101, 102, may thus be pushed over the guide wire 114 so that the first and second supports 101, 102, are guided into a similar coiled configuration as the guide wire 114, as illustrated in the example of FIGS. 2a-d. The method 200 may comprise advancing 2011' a sheath 115 and the first and second support rings 101, 102, arranged inside the sheath 115, over the guide wire 114 to assume respective coiled shapes thereof at the opposite sides of the valve, as schematically illustrated in FIGS. 2a-d.

The method 200 may subsequently comprise retracting 2012 the guide wire 114, as schematically illustrated in FIGS. 3a-d, leaving an open interior channel 105. The method 200 may comprise subsequently inserting 202 the stiffening unit 104 into the interior channel 105, as schematically illustrated in FIGS. 4a-d. The sheath 115 may be retracted as illustrated in FIGS. 5a-d, exposing the first and second rings 101, 102, in case the first and second rings 101, 102, have been inserted with a surrounding sheath 115 over the guide wire 114. The retraction of the sheath 115 may be done simultaneously as the stiffening unit 114 is inserted into the interior channel 105. The method 200 thus provides for a facilitated and secure positioning of the annuloplasty device 100 at the opposite sides of the heart valve to pinch the leaflets thereof with an increased retention force, as described above. The rings 101, 102, may be positioned with a reduced risk of entanglement in the anatomy, such as the chordae.

The method 200 may comprise activating 203 a contracted state of the annuloplasty device 100 so that a first pitch distance ($p_1$) between the first and second support rings 101, 102, in a first configuration is reduced to a second pitch distance ($p_2$) being shorter than the first pitch distance, as illustrated in FIGS. 8a-b. Thus, the first and second support rings 101, 102, move towards eachother to pinch the native heart valve leaflets. The contracted state may be activated by the insertion of the stiffening unit 104 into the interior channel 105, as described, whereby the first and second support rings 101, 102, transfer from the first configuration to the contracted state.

As elucidated above, positioning the first and second support rings 101, 102, may comprise positioning 2010 a sheath 115 to form first 116 and second 116' curves thereof as a coiled shape on the opposite sides of the native heart valve leaflets, as schematically illustrated in e.g. FIG. 2c. The sheath 115 may be advanced over a guidewire 114. The first and second support rings 101, 102, may then be advanced into the sheath 115, i.e. into first 116 and second 116' curves thereof. It is also conceivable that the guide wire 114 is retracted before the first and second support rings 101, 102, are advanced into position in the sheath 115. Further, it is also conceivable that two different guidewires 114 are used, having different stiffnesses. E.g. A first flexible guide wire may be used to guide the sheath 115 into the coiled configuration as explained. A second guide wire, being more rigid than the first guide wire may then be inserted into the coiled sheath 115 after the first flexible guide wire has been withdrawn. The second guidewire, having an increased stiffness, may facilitate the positioning of the first and second support rings 101, 102, which may then be advanced over the second guidewire for positioning in the sheath 115 in a coiled configuration at the opposite sides of the valve.

The method 200 may comprise ejecting 2013 the first and second support rings 101, 102, from the sheath 115 while retracting 2013' the sheath 115 such that the annuloplasty device 100 is arranged along the first and second curves 116, 116', on the opposite sides. The first and second support rings 101, 102, may thus be kept substantially stationary in relation to the heart valve when being ejected from the sheath 115 while simultaneously retracting the sheath 115. It is conceivable that the method 200 comprise positioning the first and second rings 101, 102, at the opposite sides without a guide wire 114. The sheath 115 may thus in this case define a path for the annuloplasty device 100 that allows for facilitated positioning thereof without having to push the first and second rings 101, 102, into position at the valve, which may otherwise be the case when the delivery catheter is kept stationary and the implant is ejected from the catheter. This also provides for an atraumatic positioning of the annuloplasty device 100.

As described above, retention units 106, 106', may be arranged on the first and/or second support rings 101, 102. The retention units 106, 106, may thus be engaged 204 of forced into tissue of the heart valve from the opposite sides when the sheath 115 is retracted, as illustrated in e.g. FIG. 6c. The sheath 115 may thus provide for protecting the tissue from the retention units 106, 106', while the rings 101, 102, are being placed into the correct position, and subsequently expose the retention units 106, 106', when gradually retracted.

The method 200 may comprise forcing 205 the retention units 106, 106', into the tissue by the insertion of the stiffening unit 104 into the interior channel 105. This provides for further increasing the retention of the annuloplasty device 100 at the heart valve as described above.

The retention units 106, 106', may comprise a shape-memory material, and the method 200 may comprise activating 204' the shape-memory material to cause the retention units 106, 106', to transfer from a retracted state (FIGS. 2e-f), in which the retention units 106, 106', are flush with an outer surface 108 of the first and/or second support rings 101, 102, to an expanded state (FIGS. 6a-c), in which the retention units 106, 106', protrudes form the outer surface 108 of the first and/or second support rings 101, 102. As described, the shape-memory material may comprise a material which is responsive to temperature, and increasing the temperature may cause the retention units 106, 106', to expand. The expansion of the retention units 106, 106', may start already when positioned inside the sheath 115 when arranged in the body.

As mentioned, the opposite sides may be an atrial side of the heart and a ventricular side of the heart. A first curve 116 of the sheath 115 may be arranged along an annulus of the heart valve on the atrial side, and a second curve 116' of the sheath 115 may be arranged around chordae of the heart valve on the ventricular side.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty device comprising
   first and second support rings being configured to be arranged as a coil in a first configuration around an axial direction, wherein the first and second support rings are configured to be arranged on opposite sides of native heart valve leaflets of a heart valve,
   a stiffening unit, wherein at least part of the first and second support rings comprises an interior channel configured to receive the stiffening unit, and
   retention units integrated with the first and/or second rings,
   wherein insertion of the stiffening unit into the interior channel increases the stiffness of the first and/or second support rings,
   wherein the retention units comprise a shape-memory material, wherein activation of the shape memory material causes the retention units to transfer from a retracted state, in which the retention units are flush with an outer surface of the first and/or second support rings, to an expanded state, in which the retention units protrude from the outer surface of the first and/or second support rings.

2. The annuloplasty device according to claim 1,
   wherein the first and second support rings are separated with a first pitch distance ($p_1$) in the axial direction, in a first configuration,
   wherein the first and second support rings are configured to assume a contracted state having a second pitch distance ($p_2$) in the axial direction being shorter than the first pitch distance, and
   wherein the first and second support rings are configured to be transferable between the first configuration and the contracted state to pinch the heart valve leaflets.

3. The annuloplasty device according to claim 2, wherein insertion of the stiffening unit into the interior channel causes the first and second support rings to transfer from the first configuration to the contracted state.

4. The annuloplasty device according to claim 2, wherein the stiffening unit comprises a shape-memory material, wherein activation of the shape memory material causes the first and second support rings to transfer from the first configuration to the contracted state.

5. The annuloplasty device according to claim 4, wherein the shape-memory material is configured to be activated in response to an activation temperature.

6. The annuloplasty device according to claim 1, wherein the first and/or second support rings are formed from a material into a tubular shape with circumferential walls enclosing said interior channel, wherein the retention units are formed from the material of the circumferential walls.

7. The annuloplasty device according to claim 1, wherein the shape-memory material is configured to assume the expanded state in response to an activation temperature.

8. Annuloplasty The annuloplasty device according to claim 1, wherein the first support ring comprises first retention units, wherein the second support ring comprises second retention units, wherein the first and second retention units extend from respective first and second retention portions to produce a retention force, in use, at both of said opposite sides.

9. The annuloplasty device according to claim 8, wherein the first support ring is adapted to be arranged on an atrial side of said heart valve, and the second support ring is adapted to be arranged on a ventricular side of the heart valve,
   wherein the first support ring comprises a first posterior bow and the second support ring comprises a second posterior bow, wherein the first and second posterior bows are adapted to conform to a posterior aspect of said heart valve, and wherein the first and second posterior bows are separated by an intermediate anterior portion,
   wherein the first and second retention units are arranged with an off-set distance from the anterior portion towards respective first and second posterior bows, whereby the anterior portion comprises a smooth surface free from retention units.

10. The annuloplasty device according to claim 1, wherein the first retention units and/or the second retention units are movable relative a normal axis (N') of surface of the first and/or second supports to which the first retention units and/or the second retention units are fixed.

11. The annuloplasty device according to claim 1, wherein the stiffening unit is attached to the first and/or second support ring.

12. The annuloplasty device according to claim 11, wherein the stiffening unit is fixed to a circumferential wall enclosing the interior channel.

13. A method of repairing a defective heart valve, comprising
    positioning first and second support rings of an annuloplasty device in a first configuration as a coil on opposite sides of native heart valve leaflets of the heart valve, said positioning comprising
    arranging a guidewire as a coil at the opposite sides of the native heart valve leaflets and
    advancing a sheath over the guidewire to form first and second curves of the sheath as a coiled shape on the opposite sides of the native heart valve leaflets, wherein the first and second support rings are arranged inside the sheath to assume a coiled shape on the opposite sides of the native heart valve leaflets,
    said method further comprising
    ejecting the first and second support rings from the sheath while retracting the sheath such that the annuloplasty device is arranged along the first and second curves on the opposite sides,
    wherein the first and second support rings are kept substantially stationary in relation to the heart valve when being ejected from the sheath while simultaneously retracting the sheath, whereby retention units arranged on the first and second support rings are engaged into tissue of the heart valve from the opposite sides when the sheath is retracted and
    wherein the opposite sides are an atrial side of the heart and a ventricular side of the heart, wherein a first curve of the sheath is arranged along an annulus of the heart valve on the atrial side, and wherein a second curve of the sheath is arranged around chordae of the heart valve on the ventricular side.

14. The method according to claim 13, comprising activating a contracted state of the annuloplasty device so that a first pitch distance ($p_1$) between the first and second support rings in a first configuration is reduced to a second pitch distance ($p_2$) being shorter than the first pitch distance, whereby the first and second support rings move towards each other to pinch the native heart valve leaflets.

15. The method according to claim 13, wherein the retention units comprise a shape-memory material, the method comprising activating the shape-memory material to cause the retention units to transfer from a retracted state, in which the retention units are flush with an outer surface of the first and/or second support rings, to an expanded state, in which the retention units protrudes form the outer surface of the first and/or second support rings.

16. The method of claim 13, wherein the sheath is embodied as a delivery catheter.

17. The method of claim 13, further comprising removing the guidewire before ejecting the first and second support rings from the sheath.

* * * * *